(12) United States Patent
Wakabayashi et al.

(10) Patent No.: US 12,272,225 B2
(45) Date of Patent: Apr. 8, 2025

(54) INFORMATION PROCESSING SYSTEM, INFORMATION PROCESSING APPARATUS, INFORMATION PROCESSING METHOD, AND NON-TRANSITORY COMPUTER-READABLE MEDIUM

(71) Applicant: PARAMOUNT BED CO., LTD., Tokyo (JP)

(72) Inventors: Masahiro Wakabayashi, Kanagawa (JP); Kazuhiro Kakehata, Kanagawa (JP); Tsutomu Mieno, Kanagawa (JP); Haruhiko Yamabuchi, Kanagawa (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 59 days.

(21) Appl. No.: 18/039,935

(22) PCT Filed: Dec. 2, 2021

(86) PCT No.: PCT/JP2021/044331
§ 371 (c)(1),
(2) Date: Jun. 1, 2023

(87) PCT Pub. No.: WO2022/124198
PCT Pub. Date: Jun. 16, 2022

(65) Prior Publication Data
US 2024/0038045 A1 Feb. 1, 2024

(30) Foreign Application Priority Data

Dec. 10, 2020 (JP) .................. 2020-204674

(51) Int. Cl.
*G08B 21/04* (2006.01)
*G06V 20/52* (2022.01)
*G06V 40/20* (2022.01)

(52) U.S. Cl.
CPC ......... *G08B 21/0476* (2013.01); *G06V 20/52* (2022.01); *G06V 40/23* (2022.01); *G08B 21/0423* (2013.01)

(58) Field of Classification Search
USPC ........................................................ 348/143
See application file for complete search history.

(56) References Cited

U.S. PATENT DOCUMENTS

2017/0016221 A1  1/2017  Yamamoto et al.
2017/0303901 A1  10/2017  Sekine
(Continued)

FOREIGN PATENT DOCUMENTS

JP  H08-187204 A  7/1996
JP  H11-341474 A  12/1999
(Continued)

OTHER PUBLICATIONS

International Search Report for PCT Application No. PCT/JP2021/044331, mailed on Feb. 8, 2022.
(Continued)

*Primary Examiner* — Nigar Chowdhury
(74) *Attorney, Agent, or Firm* — Sughrue Mion, PLLC

(57) ABSTRACT

A system includes a sensor detecting entry/exit of a person to/from a toilet and a sensor detecting leaving/sitting on a toilet seat installed on a toilet bowl; acquires excretion information indicating at least a start and an end of excretion, based on imaging data captured by an image capture apparatus installed in such a way as to include, in an image capture range, an excretion range of excrement in the bowl; authenticates a person performed entry/exit, and determines whether the person is a person to be assisted as a user of the toilet or a helper; outputs notification information to a notification destination, based on a detection event indicated by the excretion information, entry/exit information, leav- (Continued)

ing/sitting information, and an authentication result, and a notification condition; and stores, as the notification condition, necessity of notification, and the notification information and the notification destination when notification is necessary, for each events.

12 Claims, 15 Drawing Sheets

(56) References Cited

U.S. PATENT DOCUMENTS

| | | | | |
|---|---|---|---|---|
| 2018/0177158 | A1* | 6/2018 | Yamaguchi | A61B 5/02438 |
| 2020/0042780 | A1* | 2/2020 | Hori | A01K 1/0107 |
| 2020/0236897 | A1* | 7/2020 | Hori | A01K 29/005 |
| 2022/0237906 | A1 | 7/2022 | Ueda et al. | |

FOREIGN PATENT DOCUMENTS

| | | |
|---|---|---|
| JP | 2000-237098 A | 9/2000 |
| JP | 2006059185 A | 3/2006 |
| JP | 2006-330952 A | 12/2006 |
| JP | 2008-048934 A | 3/2008 |
| JP | 2008136559 A | 6/2008 |
| JP | 2009-243098 A | 10/2009 |
| JP | 2011-066632 A | 3/2011 |
| JP | 2015-136386 | 7/2015 |
| JP | 2016-021107 A | 2/2016 |
| JP | 2016031750 A | 3/2016 |
| JP | 2019-194796 A | 11/2019 |
| JP | 2019-212051 A | 12/2019 |
| JP | 2020-190181 A | 11/2020 |
| WO | 2015/087541 A1 | 6/2015 |
| WO | 2018/230104 A1 | 12/2018 |

OTHER PUBLICATIONS

European Search Report dated Sep. 12, 2024 for the corresponding European Application No. EP21903302.4.

* cited by examiner

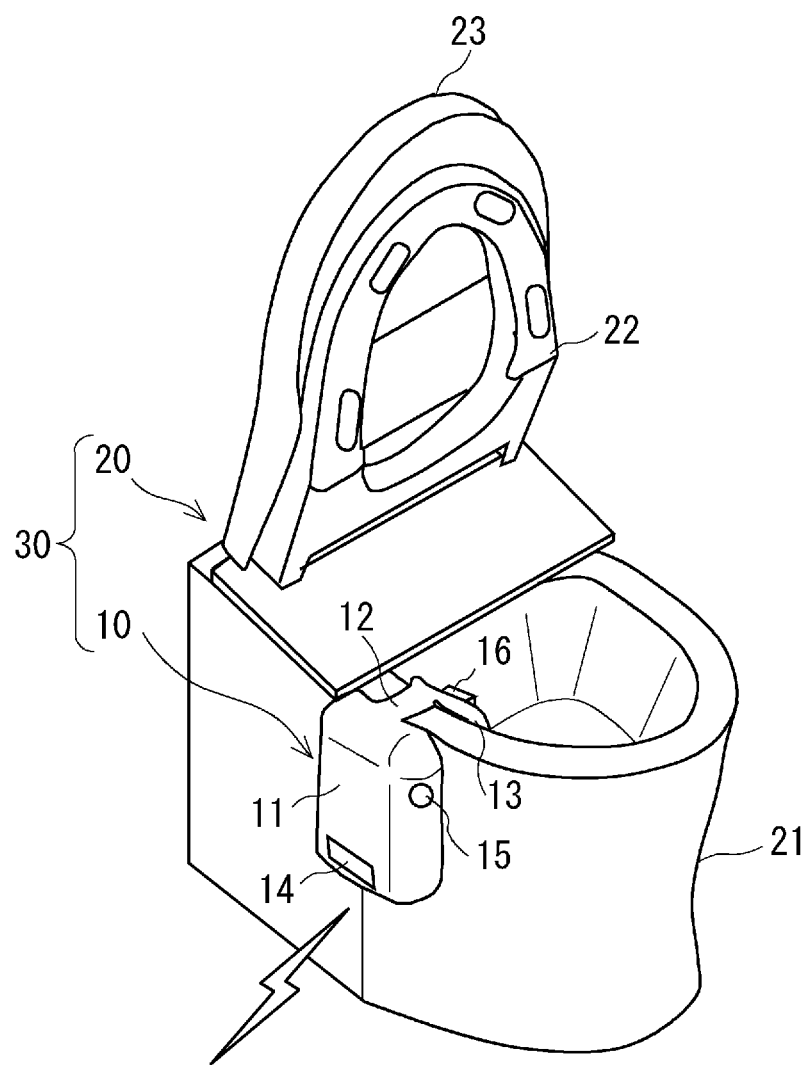
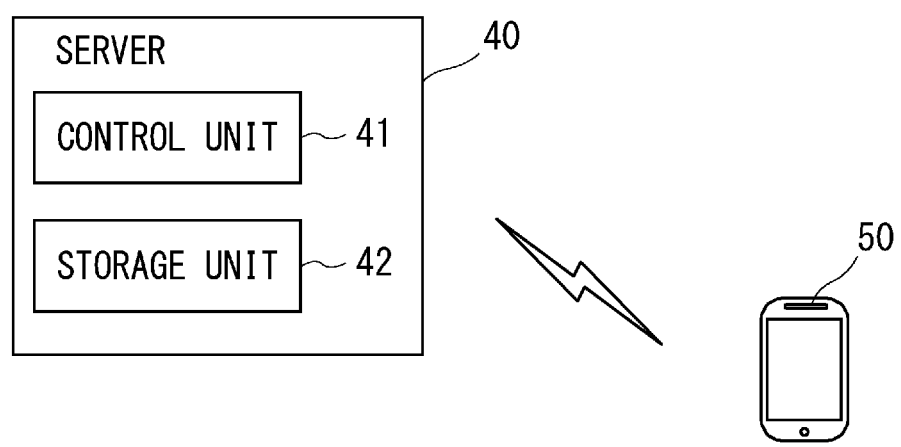
Fig. 2

Fig. 6

| No. | TOILET USE NOTIFICATION | ASSISTANCE-IN-PROGRESS NOTIFICATION FILTER TARGET/NON-TARGET | NOTIFICATION CONDITION |
|---|---|---|---|
| 1 | CARE RECIPIENT TOILET ENTRY NOTIFICATION | TARGET | NOTIFY WHEN ASSISTANCE STATE IS NOT ASSISTANCE IN PROGRESS |
| 2 | CARE RECIPIENT TOILET SITTING NOTIFICATION | TARGET | NOTIFY WHEN ASSISTANCE STATE IS NOT ASSISTANCE IN PROGRESS |
| 3 | CARE RECIPIENT TOILET EXCRETION START NOTIFICATION | TARGET | NOTIFY WHEN ASSISTANCE STATE IS NOT ASSISTANCE IN PROGRESS |
| 4 | CARE RECIPIENT TOILET EXCRETION END NOTIFICATION | TARGET | NOTIFY WHEN ASSISTANCE STATE IS NOT ASSISTANCE IN PROGRESS |
| 5 | CARE RECIPIENT TOILET LEAVING NOTIFICATION | TARGET | NOTIFY WHEN ASSISTANCE STATE IS NOT ASSISTANCE IN PROGRESS |
| 6 | CARE RECIPIENT TOILET EXIT NOTIFICATION | TARGET | NOTIFY WHEN ASSISTANCE STATE IS NOT ASSISTANCE IN PROGRESS |
| 7 | CARE RECIPIENT TOILET LONG-TIME SITTING NOTIFICATION | TARGET | NOTIFY WHEN ASSISTANCE STATE IS NOT ASSISTANCE IN PROGRESS |
| 8 | FOREIGN BODY DETECTION IN TOILET BOWL NOTIFICATION | NON-TARGET | NOTIFY REGARDLESS OF ASSISTANCE STATE |
| 9 | EXCRETION IDENTIFICATION SENSOR DIRTY NOTIFICATION | NON-TARGET | NOTIFY REGARDLESS OF ASSISTANCE STATE |
| 10 | SERVICE RECOVERY NOTIFICATION | NON-TARGET | NOTIFY REGARDLESS OF ASSISTANCE STATE |
| 11 | CAREGIVER TOILET ENTRY NOTIFICATION | TARGET | NOTIFY WHEN ASSISTANCE STATE IS NOT ASSISTANCE IN PROGRESS |
| 12 | CAREGIVER TOILET EXIT NOTIFICATION | TARGET | NOTIFY WHEN ASSISTANCE STATE IS NOT ASSISTANCE IN PROGRESS |
| 13 | CAREGIVER RUSH NOTIFICATION | TARGET | NOTIFY WHEN ASSISTANCE STATE IS NOT ASSISTANCE IN PROGRESS |
| 14 | CAREGIVER RUSH STOP NOTIFICATION | TARGET | NOTIFY WHEN ASSISTANCE STATE IS NOT ASSISTANCE IN PROGRESS |

Fig. 7

| No. | TOILET USE NOTIFICATION | NOTIFICATION TYPE SETTING TARGET/NON-TARGET | NOTIFICATION CONDITION |
|---|---|---|---|
| 1 | CARE RECIPIENT TOILET ENTRY NOTIFICATION | TARGET | SET ACCORDING TO STATE OF CARE RECIPIENT |
| 2 | CARE RECIPIENT TOILET SITTING NOTIFICATION | TARGET | SET ACCORDING TO STATE OF CARE RECIPIENT |
| 3 | CARE RECIPIENT TOILET EXCRETION START NOTIFICATION | TARGET | SET ACCORDING TO STATE OF CARE RECIPIENT |
| 4 | CARE RECIPIENT TOILET EXCRETION END NOTIFICATION | TARGET | SET ACCORDING TO STATE OF CARE RECIPIENT |
| 5 | CARE RECIPIENT TOILET LEAVING NOTIFICATION | TARGET | SET ACCORDING TO STATE OF CARE RECIPIENT |
| 6 | CARE RECIPIENT TOILET EXIT NOTIFICATION | TARGET | SET ACCORDING TO STATE OF CARE RECIPIENT |
| 7 | CARE RECIPIENT TOILET LONG-TIME SITTING NOTIFICATION | NON-TARGET | FIX TO ALERT NOTIFICATION |
| 8 | FOREIGN BODY DETECTION IN TOILET BOWL NOTIFICATION | NON-TARGET | FIX TO ALERT NOTIFICATION |
| 9 | EXCRETION IDENTIFICATION SENSOR DIRTY NOTIFICATION | NON-TARGET | FIX TO ALERT NOTIFICATION |
| 10 | SERVICE RECOVERY NOTIFICATION | NON-TARGET | FIX TO NORMAL NOTIFICATION |
| 11 | CAREGIVER TOILET ENTRY NOTIFICATION | NON-TARGET | FIX TO NORMAL NOTIFICATION |
| 12 | CAREGIVER TOILET EXIT NOTIFICATION | NON-TARGET | FIX TO NORMAL NOTIFICATION |
| 13 | CAREGIVER RUSH NOTIFICATION | NON-TARGET | FIX TO NORMAL NOTIFICATION |
| 14 | CAREGIVER RUSH STOP NOTIFICATION | NON-TARGET | FIX TO NORMAL NOTIFICATION |

| NOTIFICATION TYPE | PURPOSE |
|---|---|
| ALERT NOTIFICATION | NOTIFICATION HAVING PURPOSE FOR CAUSING TO RUSH TO CARE RECIPIENT WHO NEEDS TO BE ASSISTED BY CAREGIVER. NOTIFICATION HAVING PURPOSE FOR NOTIFYING THAT SERVICE CANNOT PERFORM CONTINUOUS USE DUE TO APPARATUS FAILURE OR THE LIKE, AND REQUIRING IMMEDIATE HANDLING. |
| NORMAL NOTIFICATION | NOTIFICATION HAVING PURPOSE FOR CAUSING TO RECOGNIZE TOILET USE OF CARE RECIPIENT WHO DOES NOT NEED TO BE ASSISTED, AND CAUSING TO WATCH CARE RECIPIENT. |
| NOT NOTIFY | NON-NOTIFICATION HAVING PURPOSE FOR NOT NOTIFYING IN CASE OF HEALTHY PERSON OR IN CASE WHERE IT IS DETERMINED THAT NOTIFICATION ITSELF IS NOT NECESSARY FOR CARE RECIPIENT WHO DOES NOT NEED TO BE ASSISTED NOR WATCHED. |

Fig. 8

INFORMATION PROCESSING SYSTEM, INFORMATION PROCESSING APPARATUS, INFORMATION PROCESSING METHOD, AND NON-TRANSITORY COMPUTER-READABLE MEDIUM

This application is a National Stage Entry of PCT/JP2021/044331 filed on Dec. 2, 2021, which claims priority from Japanese Patent Application 2020-204674 filed on Dec. 10, 2020, the contents of all of which are incorporated herein by reference, in their entirety.

TECHNICAL FIELD

The present disclosure relates to an information processing system, an information processing apparatus, an information processing method, and a program.

BACKGROUND ART

A caregiver who provides excretion assistance at a caregiving site is required to reduce incontinence of a care receiver (care recipient) and support independence of the care receiver while maintaining dignity of the care receiver. Since the excretion assistance at a caregiving site may damage dignity of the care receiver according to occasions, a caregiver is forced to bear a heavy burden, and support for reducing a load of work is required.

The work of the caregiver also includes work of making an excretion diary in excretion assistance for the care receiver. Therefore, the caregiver acquires information to be written in the excretion diary by entering a toilet with a care receiver and observing an excretion behavior of the care receiver, or hearing from the care receiver. However, since observing excretion behavior is a shame for the care receiver, it can be said that a scene in which dignity of the care receiver is damaged is easy to occur, and observation in such a scene is a task that imposes a burden on the caregiver.

In addition, when a care receiver has dementia, the care receiver may mistake a diaper or a urine absorbing pad as toilet paper during excretion, or intentionally try to hide an evidence of excretion failure (incontinence of feces and urine) due to his/her shame. Then, in such a case, behavior of flushing a diaper or a urine absorbing pad to the toilet may be performed. In such a case or on a regular basis, a care facility asks a contractor to perform a drain pipe cleaning work such as foreign body removal in order to clear clogging of a drain pipe.

In addition, in a case where assistance is required for leaving a toilet seat or exiting from the toilet, or in order to prevent an unexpected situation in the toilet, a caregiver needs to clearly assist before and after excretion behavior, and thereby a burden on the caregiver increases. In addition, there is a case where recognizing constipation and dysuria is difficult and then detection is delayed, or a case where unnecessary medication is increased due to symptomatic therapy.

With regard to recording of defecation, Patent Literature 1 describes a toilet sensor apparatus in which a defecation record of a care recipient is automatically collected, and a use time and the number of times of use of a toilet are reliably recorded even when a demented elderly person or a child performs defecation by himself/herself in a facility such as a hospital or a nursing home. The toilet sensor apparatus described in Patent Literature 1 includes a detection means for outputting a detection signal to a data processing means when detecting that a user is sitting on a toilet seat, and a data processing means connected to the detection means. The data processing means described above stores the number of times of use of the toilet by a user and a preset reference time T1 serving as a reference for a use time of the toilet by a user, determines whether the user is sitting on the toilet seat, based on a detection signal from the detection means, and measures a use time T2 during which the user is sitting on the toilet seat. When the measured use time T2 exceeds the reference time T1, the data processing means described above adds 1 to the stored use count and stores the added use count as a new use count, and displays the stored new use count. With regard to notification of abnormality, Patent Literature 2 describes a monitoring apparatus that switches a notification destination and a notification content after first notification according to a type of abnormality occurring on a care recipient. The monitoring apparatus described in Patent Literature 2 is an apparatus being connectable to a plurality of communication terminal apparatuses via a network, and includes an imaging means, a detection means for detecting abnormality, a reception means for receiving information from the plurality of communication terminal apparatuses, and a transmission means. When abnormality is detected by the detection means, the transmission means transmits first transmission information being generated for each communication terminal apparatus, based on the transmission control file, to a plurality of communication terminal apparatuses described in the transmission control file. In addition, when information is received by the reception means from one of the plurality of communication terminal apparatuses that transmits the first transmission information, the transmission means transmits second transmission information being generated based on the transmission control file to the communication terminal apparatus described in the transmission control file.

With regard to detection of an operation of a user of a toilet, Patent Literature 3 describes a toilet seat apparatus having a purpose for accurately detecting various operations of a human body, such as entering into a toilet, exiting from a toilet, sitting on a toilet seat, and leaving a toilet seat.

CITATION LIST

Patent Literature

[Patent Literature 1] Japanese Unexamined Patent Application Publication No. 2000-237098
[Patent Literature 2] Japanese Unexamined Patent Application Publication No. 2011-066632
[Patent Literature 3] International Patent Publication No. WO2015/087541

SUMMARY OF INVENTION

As described above, a caregiver performs excretion management and excretion assistance of a care recipient, but there are the following problems in performing work.

First, a caregiver monitors toilet use status of a care recipient in order to perform excretion management and excretion assistance. The caregiver is in charge of a plurality of care recipients by himself/herself, and although priority varies depending on a degree of care, the caregiver monitors a toilet in order to recognize use status of the toilet and provide assistance. Therefore, the caregiver stands by in a place where status of the care recipient can be confirmed, and when the care recipient moves, the caregiver goes to confirm whether the care recipient uses the toilet. When a destination of the care recipient is a toilet, the caregiver will attend for assistance, but when not a toilet, the caregiver needs to return to confirm status of another care recipient, which is labor-intensive. In addition, when a care recipient who needs assistance before and after excretion is using a toilet, the caregiver needs to wait in the toilet or near the toilet until excretion of the care recipient is completed, and provide necessary assistance for each care recipient. Therefore, since a trend of another care recipient in charge cannot be confirmed, it is necessary to confirm status of the another care recipient after the care assistance, and to confirm whether using the toilet when the another care recipient is not in a room. As described above, there is a problem that the caregiver has a long time to concern with monitoring the toilet of the care recipient, and the caregiver does not have time for other work.

Secondly, a care recipient who is difficult in independent excretion needs to be assisted by a caregiver when excretion is performed, but when the caregiver is not in the vicinity, the care recipient may go to a toilet alone. When a care recipient enters the toilet alone, it is necessary to wait for rushing of the caregiver to perform excretion, but when the caregiver does not notice the toilet entry while assisting another care recipient, or when the caregiver does not know and looks for in which toilet the care recipient enters, the caregiver cannot immediately rush for assistance. Therefore, there is a problem that a situation in which the care recipient keeps waiting until the caregiver rushes, and leaks in the toilet may occur. In addition, there is a problem that a situation in which a care recipient is injured by falling while moving to a toilet seat or a situation in which a care recipient is injured by falling by breaking a balance when the care recipient stands up while trying to take off his/her clothes may occur due to trying to perform excretion by himself/herself before the caregiver rushes. In addition, there is also a problem of a situation in which excretion is not completed because assistance during the excretion is not performed. In addition, when the caregiver provides assistance before excretion and is not present in the toilet during the excretion, the caregiver does not notice an end of the excretion and does not provide assistance when the care recipient cannot inform the end of the excretion to the caregiver, and thus there is a problem that the care recipient remains sitting. Further, when abnormality occurs during excretion of the care recipient and is not informed to the caregiver, there is a problem that the caregiver does not notice a state of the care recipient, and cannot immediately respond. In addition, when a care recipient who is difficult to walk leaves the toilet seat or exits from the toilet, the caregiver needs to perform assistance in order to move, but when the caregiver is not nearby, there is a problem that the care recipient continues to wait in the vicinity of the toilet. In this way, there is a problem that occurs due to being unable to receive assistance in the toilet for a care recipient, such as when the care recipient enters the toilet alone or when the caregiver does not notice status of the care recipient.

Thirdly, when a caregiver notices a toilet use by a care recipient and rushes in order to perform assistance, there is a problem that rushing for assistance is wasted since status of another caregiver, such as when the care recipient is already assisted by another caregiver, or when caregivers rush more than necessary, is not known. In addition, there is a problem that, when a plurality of caregivers are required, other caregivers do not rush, and thereby it takes time to assist the care recipient. As described above, there is a problem caused by a case where the status cannot be shared among caregivers.

Fourthly, the caregiver records excretion status of a care recipient, but as described above, in order to record the excretion status, it is necessary to directly confirm excretion behavior by attending the toilet when the care recipient uses the toilet, or to hear the care recipient later, which is a burden on the caregiver. In addition, it is necessary for a caregiver to regularly promote excretion because some care recipients do not feel urinary intention or fecal intention, but it takes time and effort to hear the excretion status from the care recipient or to confirm the excretion status from an excretion record, which is a burden on the caregiver. As described above, there is a problem in a case where the caregiver confirms the excretion status of the care recipient.

Fifthly, as described above, a care recipient may mistake a diaper or a urine absorbing pad as toilet paper and flush it to the toilet during excretion, or may flush a diaper or a urine absorbing pad to the toilet in order to hide failure of excretion by the care recipient. Therefore, it is necessary for a care facility to periodically ask a piping contractor to perform foreign body removal, and there is a problem that a facility related to drainage cannot be operated during the work.

In order to improve the above status, a mechanism in which a toilet sensor is installed and the toilet sensor notifies a caregiver of toilet use status of a care recipient as necessary is desired. Note that, the techniques described in Patent Literatures 1 to 3 cannot solve the above-described problems because information on whether a caregiver is assisting a care recipient in the toilet cannot be acquired.

The present disclosure is made for solving the above-described problems, and provides an information processing system, an information processing apparatus, an information processing method, and a program that are capable of notifying a caregiver of use status of a toilet of a care recipient according to care status by the caregiver.

An information processing system according to a first aspect of the present disclosure includes an acquisition unit, a first sensor, a second sensor, an authentication unit, a storage unit, and an output unit. The acquisition unit acquires excretion information indicating at least a start and an end of excretion, based on imaging data captured by an image capture apparatus installed in such a way as to include, in an image capture range, an excretion range of excrement in a toilet bowl of a toilet. The first sensor detects entry/exit of a person to/from the toilet. The second sensor detects leaving and sitting on a toilet seat installed on the toilet bowl. The authentication unit authenticates a person who has performed entry/exit to/from the toilet, and also determines whether the person is a person to be assisted as a user of the toilet or a helper who assists the user. The storage unit stores a notification condition. The output unit outputs notification information to a notification destination, based on a detection event indicated by the excretion information acquired by the acquisition unit, entry/exit information detected by the first sensor, leaving/sitting information detected by the second sensor, and an authentication result in the authentication unit, and the notification condition. The storage unit stores, as the notification condition, necessity of notification, and the notification information and the notification destination when notification is necessary, for each of the detection events.

An information processing apparatus according to a second aspect of the present disclosure is an information processing apparatus that includes an image capture apparatus, and is installed in a toilet bowl in such a way that the image capture apparatus is arranged in such a way as to include, in an image capture range, an excretion range of excrement in the toilet bowl of a toilet. The information processing apparatus includes an acquisition unit, a first sensor, a second sensor, an authentication unit, a storage unit, and an output unit. The acquisition unit acquires excretion information indicating at least a start and an end of excretion, based on imaging data captured by the image capture apparatus. The first sensor detects entry/exit of a person to/from the toilet. The second sensor detects leaving and sitting on a toilet seat installed on the toilet bowl. The authentication unit authenticates a person who has performed entry/exit to/from the toilet, and also determines whether the person is a person to be assisted as a user of the toilet or a helper who assists the user. The storage unit stores a notification condition. The output unit outputs notification information to a notification destination, based on a detection event indicated by the excretion information acquired by the acquisition unit, entry/exit information detected by the first sensor, leaving/sitting information detected by the second sensor, and an authentication result in the authentication unit, and the notification condition. The storage unit stores, as the notification condition, necessity of notification, and the notification information and the notification destination when notification is necessary, for each of the detection events.

An information processing method according to a third aspect of the present disclosure includes an acquisition step, a first detection step, a second detection step, an authentication step, a storage step, and an output step. The acquisition step acquires excretion information indicating at least a start and an end of excretion, based on imaging data captured by an image capture apparatus installed in such a way as to include, in an image capture range, an excretion range of excrement in a toilet bowl of a toilet. In the first detection step, a first sensor detects entry/exit of a person to/from the toilet. In the second detection step, a second sensor detects leaving and sitting on a toilet seat installed on the toilet bowl. The authentication step authenticates a person who has performed entry/exit to/from the toilet, and also determines whether the person is a person to be assisted as a user of the toilet or a helper who assists the user. The storage step stores a notification condition. The output step outputs notification information to a notification destination, based on a detection event indicated by the excretion information acquired in the acquisition step, entry/exit information detected by the first sensor, leaving/sitting information detected by the second sensor, and an authentication result in the authentication step, and the notification condition. The storage step stores, as the notification condition, necessity of notification, and the notification information and the notification destination when notification is necessary, for each of the detection events.

A program according to a fourth aspect of the present disclosure is a program for causing a computer to execute processing including an acquisition step, a first detection step, a second detection step, an authentication step, a storage step, and an output step. The acquisition step acquires excretion information indicating at least a start and an end of excretion, based on imaging data captured by an image capture apparatus installed in such a way as to include, in an image capture range, an excretion range of excrement in a toilet bowl of a toilet. The first detection step detects, by a first sensor, entry/exit of a person to/from the toilet. The second detection step detects, by a second sensor, leaving and sitting on a toilet seat installed on the toilet bowl. The authentication step authenticates a person who has performed entry/exit to/from the toilet, and also determines whether the person is a person to be assisted as a user of the toilet or a helper who assists the user. The storage step stores a notification condition. The output step outputs notification information to a notification destination, based on a detection event indicated by the excretion information acquired in the acquisition step, entry/exit information detected by the first sensor, leaving/sitting information detected by the second sensor, and an authentication result in the authentication step, and the notification condition. The storage step stores, as the notification condition, necessity of notification, and the notification information and the notification destination when notification is necessary, for each of the detection events.

According to the present disclosure, it is possible to provide an information processing system, an information processing apparatus, an information processing method, and a program that are capable of notifying a caregiver of use status of a toilet of a care recipient according to care status by the caregiver.

BRIEF DESCRIPTION OF DRAWINGS

FIG. 2 is a diagram illustrating one configuration example of an information processing system according to a second example embodiment;

FIG. 6 is a diagram illustrating an example of a notification condition in the information processing system in FIG. 2;

FIG. 7 is a diagram illustrating an example of a notification type and a setting content in the notification condition in FIG. 6;

FIG. 8 is a diagram illustrating a purpose of the notification type in FIG. 7;

EXAMPLE EMBODIMENT

Hereinafter, example embodiments will be described with reference to the drawings. Note that, in the example embodiments, the same or equivalent elements may be denoted by the same reference signs, and redundant description will be omitted as appropriate.

First Example Embodiment

Figure 1:
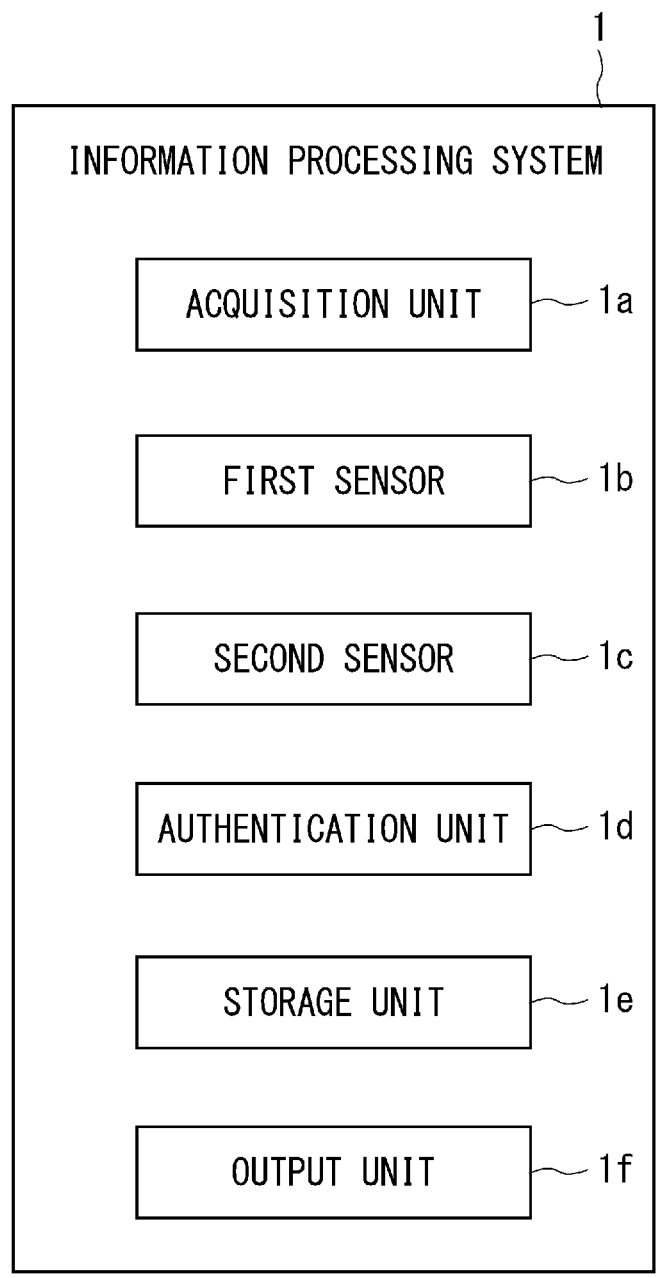
FIG. 1 is a block diagram illustrating one configuration example of an information processing system according to a first example embodiment.

FIG. 1 is a block diagram illustrating one configuration example of an information processing system according to a first example embodiment.

As illustrated in FIG. 1, an information processing system 1 according to the present example embodiment can include an acquisition unit 1a, a first sensor 1b, a second sensor 1c, an authentication unit 1d, a storage unit 1e, and an output unit 1f.

The acquisition unit 1a acquires excretion information, based on imaging data captured by an image capture apparatus (hereinafter, exemplified as a camera) installed in such a way as to include, in an image capture range, an excretion range of excrement in a toilet bowl of a toilet. Therefore, the information processing system 1 is connected to or includes a camera installed in this way. The camera is not limited to a visible light camera, and may be an infrared light camera and the like, or may be a video camera as long as a still image can be extracted.

The excretion range described above may be an area including a stagnant part of the toilet bowl, and can also be referred to as a scheduled excretion range. By installing the camera in such a way as to include such an excretion range in the image capture range, captured imaging data includes excrement and the like as a subject. Of course, the excretion range described above is preferably set in such a way that a user of the toilet is not reflected, and the camera is preferably installed in such a way that a lens of the camera is not seen by the user. In addition, when a user uses the information processing system 1 in a hospital or a care facility, for example, the user described above is mainly a care receiver such as a patient.

The excretion information is information indicating at least a start and end of excretion. The excretion information preferably includes information indicating a content of excretion, and in a simpler example, information indicating that excrement is feces (stool) or pee (urine). In addition, the excretion information can also include other information such as information indicating a color of excrement, and a shape of a solid body when excrement is the solid body.

The acquisition unit 1a can acquire the excretion information, for example, by using a learned model or by performing comparison by image matching and the like. The learned model may be any model that outputs excretion information, based on imaging data captured by the camera, and can be stored in the storage unit 1e or another not-illustrated storage unit. For example, the learned model can be a model in which the imaging data described above is input, or data acquired by preprocessing the imaging data described above is input, and excretion information (may be a plurality of types of information) is output. Note that, a learned model may be generated by machine learning, regardless of an algorithm (algorithm of machine learning), a hyperparameter such as the number of layers. In this way, the acquisition unit 1a can acquire the excretion information by using the learned model, based on the imaging data.

On the other hand, in a configuration in which the acquisition unit 1a performs comparison such as image matching, various pieces of image data to be compared or feature data thereof may be associated with excretion information indicating a content of excretion, and stored in a not-illustrated storage unit. Then, the acquisition unit 1a may perform comparison with the data stored in the storage unit after inputting the imaging data from the camera and extracting and the like the feature thereof, and output the excretion information indicated by data to be compared which matches the data or has the highest matching rate.

In addition, the imaging data can include attached information such as an imaging date and time and an imaging condition, and the learned model can also be a model in which not only the imaging data but also other information are input as a parameter. The imaging condition can include, for example, a resolution of a camera whose resolution can be set, and a zoom magnification of a camera having a zoom function.

In addition, the imaging data used for acquiring the excretion information can be, for example, data when an object is detected as a subject in the excretion range or a change such as a change in the color of stagnant water is detected, and it can be determined that a time point at which the change occurs is a time point at which excretion starts or ends. The detection can be performed, for example, by performing imaging with a camera at all times or at regular intervals, and using imaging data acquired through the imaging. Note that, the imaging may be started based on a user detection result from a separately provided user detection sensor (a load sensor provided on a toilet seat, another human detecting sensor, or the like), and imaging data at that time can be used for acquiring excretion information.

The first sensor 1b detects entry/exit of a person to/from a toilet. The first sensor 1b may be, for example, the human detecting sensor described above.

The second sensor 1c detects leaving and sitting (sitting on and leaving from a seat) on a toilet seat installed in a toilet bowl. The second sensor 1c can be, for example, the above-described load sensor (pressure-sensitive sensor), or can be a camera, a human detecting sensor, or the like disposed except for the toilet seat. The toilet seat can be equipment having a washing function of the toilet bowl (e.g., a hot water washing toilet seat such as a washlet (registered trademark) having a function of flushing the toilet). The information processing system 1 can also include such equipment or a toilet bowl integrated with a hot water washing toilet seat.

The authentication unit 1d authenticates a person who has performed entry/exit to/from a toilet, and determines whether the person is a person to be assisted (a care recipient) as a user of the toilet or a caregiver who assists the user. Note that, a person to be assisted as a user of a toilet refers to a person when the user is a care recipient. In other words, a care recipient as a user of the toilet is referred to as a "person to be assisted" because the care recipient is assisted during use of the toilet. A care recipient is also referred to as a "care receiver". In addition, a caregiver such as a caregiver and a doctor are also referred to as a "helper" because a caregiver provide assistance while a person to be assisted uses the toilet.

For authentication as described above, the authentication unit 1d can include a person recognition sensor including a camera and a face authentication processing unit, a person recognition sensor that performs person recognition by recognizing a tag held by a person as a part of clothes, an IC card, or the like, and the like. The authentication unit 1d determines, based on a recognition result by such a person recognition sensor, whether the person who performs entry/exit to/from the toilet is a person to be assisted or a caregiver. The determination itself can be executed by referring to information, associated with a recognized person in advance, indicating a care recipient (a person who can be a person to be assisted) or a helper. Note that, a user of the toilet can also be assumed to be a person who does not fall under any of the person to be assisted and the helper (for example, a family member who has visited a sympathy, or the like), but the authentication unit 1d may determine that the user is neither the person to be assisted nor the helper in that case. In this case, an event does not correspond to any of detection events described later.

The output unit 1f outputs notification information to a notification destination, based on a detection event indicated by the excretion information acquired by the acquisition unit 1a, entry/exit information detected by the first sensor 1b, leaving/sitting information detected by the second sensor 1c, and an authentication result by the authentication unit 1d, and a notification condition. The output unit 1f can be, for example, a communication unit configured by a wired or wireless communication interface or the like. The output unit 1f can transmit the notification information to a terminal apparatus (not illustrated) of the notification destination via a communication unit, for example. For example, the output unit 1f can transmit the notification information to an external server (not illustrated) via the communication unit, and thus a server can transfer the notification information to the terminal apparatus of the notification destination.

The storage unit 1e stores a notification condition referred to by the output unit 1f. The storage unit 1e stores, as a notification condition, necessity of notification, and the notification information and the notification destination when notification is necessary, for each detection event. The number of notification destinations to be notified with respect to a certain detection event may be one, or may be plural.

The information processing system 1 can include a control unit (not illustrated), and the control unit can include the acquisition unit 1a, the authentication unit 1d, the storage unit 1e, and the output unit 1f (or a part thereof) described above. The control unit can be achieved by, for example, a central processing unit (CPU), a working memory, a non-volatile storage apparatus storing a program, and the like. The program can be a program for causing the CPU to execute processing of the acquisition unit 1a, the authentication unit 1d, the storage unit 1e, and the output unit 1f and detection processing in the first sensor 1b and the second sensor 1c. In addition, the control unit included in the information processing apparatus 1 can also be achieved by, for example, an integrated circuit.

In addition, the information processing system 1 according to the present example embodiment can be configured as a single information processing apparatus, or can be configured as a plurality of apparatuses in which functions are distributed. In the latter case, each apparatus may include a control unit, a communication unit, a storage unit as necessary, and the like, and the plurality of apparatuses may be connected to one another as necessary by wireless or wired communication and achieve a function as the information processing system 1 in cooperation with one another.

Further, the information processing system 1 may also be a configuration including the above-described image capture apparatus (camera), and when being configured as a single information processing apparatus, the information processing apparatus includes the camera. In this way, when the information processing system 1 is configured as a single information processing apparatus, it is preferred that the information processing apparatus includes the above-described camera, and is installed on a toilet bowl of a toilet in such a way that the camera is arranged in such a way as to include, in an image capture range, an excretion range of excrement in the toilet bowl. In this case, the information processing apparatus can also be referred to as a notification apparatus or an excretion information acquisition apparatus.

As described above, in the present example embodiment, it is possible to acquire, as notification information, information as to whether a caregiver, such as a caregiver, assists a care recipient in a toilet according to a detection event. Therefore, according to the present example embodiment, it is possible to notify the caregiver of use status of the toilet by the care recipient according to care status of the caregiver.

Second Example Embodiment

Figure 3:
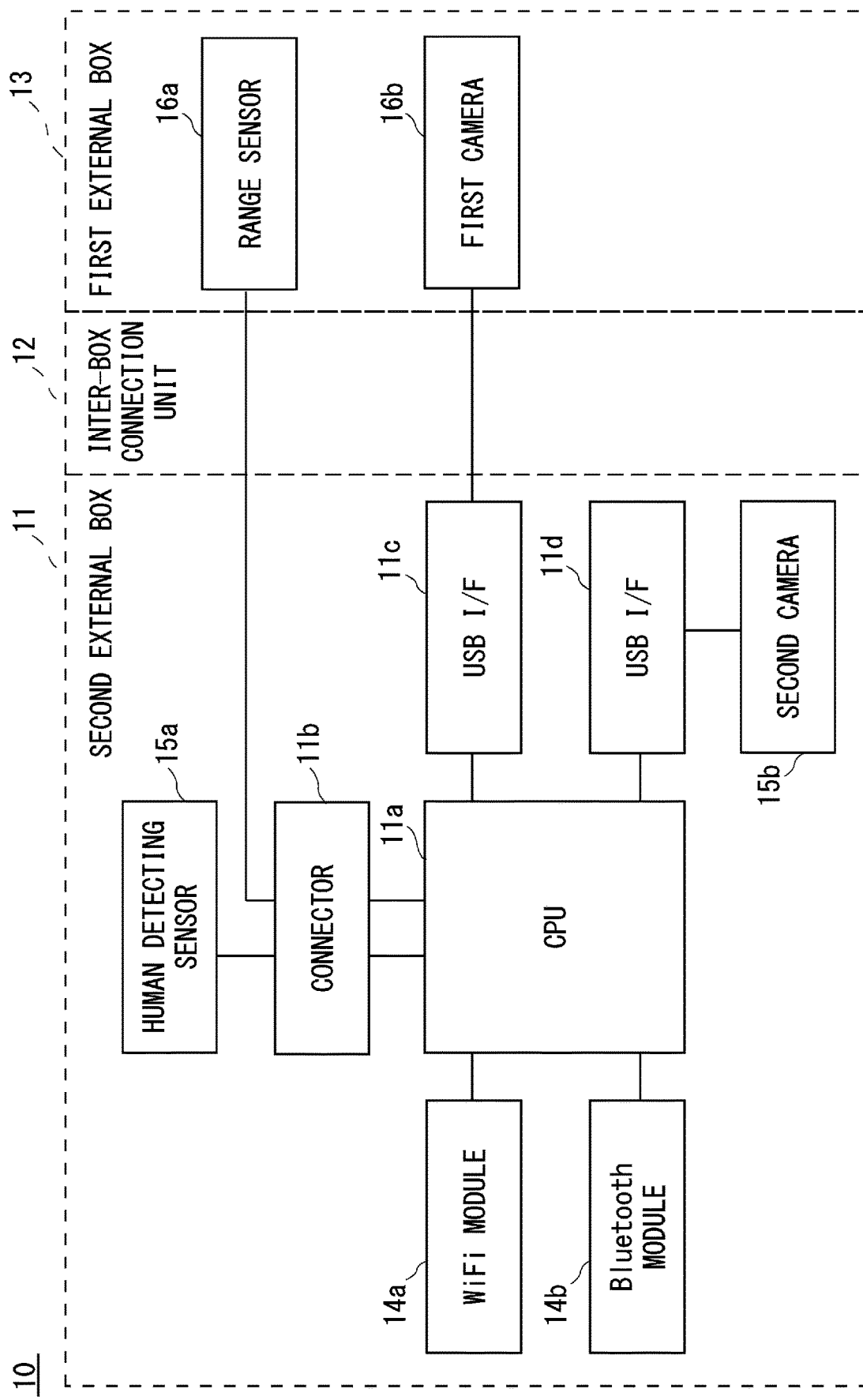
FIG. 3 is a block diagram illustrating one configuration example of an information processing apparatus in the information processing system in FIG. 2.

Although a second example embodiment will be mainly described a different point from the first example embodiment with reference to FIGS. 2 to 14, various examples described in the first example embodiment can be applied. FIG. 2 is a block diagram illustrating one configuration example of an information processing system according to the second example embodiment, and FIG. 3 is a block diagram illustrating one configuration example of an information processing apparatus in the information processing system in FIG. 2.

The information processing system according to the present example embodiment (hereinafter, the present system) can be a system in which a part of the information processing system is installed in a toilet and notifies a helper or the like, and will be described in detail below.

The present system can include an information processing apparatus 10 attached to a toilet bowl 20, a server 40 wirelessly connected to the information processing apparatus 10, and a terminal apparatus 50 wirelessly connected to the server 40. Note that, the connection can be performed in one wireless local area network (LAN), for example. In addition, in the following description, the information processing apparatus 10 is described as being installed on the toilet bowl 20 of a toilet, but at least a part of the information processing apparatus 10, such as a camera for capturing imaging data for acquiring excretion information, may be installed on the toilet bowl 20. The toilet bowl 20 can be provided, on a body 20 thereof, with, for example, a toilet seat 22 equipped with a hot water washing function for user washing or the like, and a toilet seat cover 23 for closing the toilet seat 22.

The information processing apparatus 10 can be a toilet-installation type (in this example, a toilet bowl-installation type) apparatus, and performs notification on a detection event while cooperating with the server 40 and the terminal apparatus 50. Note that, although not described in detail, the information processing apparatus 10 can be configured to record excrement, present excrement information (notification or the like), and predict excrement while cooperating with the server 40 and the terminal apparatus 50. The information processing apparatus 10 and the toilet bowl 20 can constitute, for example, a toilet bowl 30 with a function of outputting excretion information.

In addition, a shape of the information processing apparatus 10 is not limited to a shape illustrated in FIG. 2, and can be configured such that all or some of the functions of the information processing apparatus 10 are embedded in, for example, the toilet seat 22 and the like. In addition, some of the functions of the information processing apparatus 10 can be provided on a toilet seat 22 side.

Herein, before describing a detailed example of the information processing apparatus 10, a configuration associated to each unit of the information processing system 1 in FIG. 1 will be briefly described.

As an example of an image capture apparatus (camera) used in an acquisition unit 1a in FIG. 1, a first camera 16b described later may be provided in the information processing apparatus 10. Alternatively, a camera may be provided on the toilet seat 22 side, and a configuration such that the information processing apparatus 10 receives imaging data from the camera by wireless or wired communication can be adopted. As an example of a first sensor 1b in FIG. 1, the information processing apparatus 10 can be provided with a human detecting sensor 15a and/or a second camera 15b, which will be described later. The second camera 15b can also be used as a part of an authentication unit 1d in FIG. 1, and in this case, the authentication unit 1d can execute face authentication processing by using face image data captured by the second camera 15b.

As an example of a second sensor 1c in FIG. 1, a range sensor 16a described later can be provided in the information processing apparatus 10. Alternatively, as the second sensor 1c, a load sensor (a pressure-sensitive sensor such as a weight sensor) can also be provided inside the toilet seat 22 or in the information processing apparatus 10 at a position in contact with a lower surface of the toilet seat 22. When a load sensor is provided inside the toilet seat 22, information from the load sensor may be received by the information processing apparatus 10 by wireless or wired communication.

Other pieces of processing such as acquisition processing of imaging data by the camera in the acquisition unit 1a, face authentication processing in the authentication unit 1d, storage processing in the storage unit 1e, and output processing in an output unit 1f can be executed by a control unit of the information processing apparatus 10 while cooperating with the server 40 and the terminal apparatus 50 as necessary.

The server 40 can include a control unit 41 that controls the entirety of the server, and a storage unit 42 that accumulates a notification condition and various pieces of acquired information (and information generated based on the information). The control unit 41 can be achieved by, for example, a CPU, a working memory, a non-volatile storage apparatus storing a program, and the like. In addition, the control unit 41 can also be achieved by, for example, an integrated circuit. The storage apparatus can be used as the storage unit 42, and the program can be a program for causing the CPU to achieve a function of the server 40.

In addition, it is preferred that the storage unit 42 stores, as a notification condition, necessity of notification, and notification information and a notification destination when notification is necessary, for each detection event and for each person to be assisted as a user.

The terminal apparatus 50 is a terminal apparatus possessed by a helper who assists (becomes to assist) a person to be assisted as a user of a toilet, and can be a portable-type information processing apparatus, but may be an installation type apparatus. In the former case, the terminal apparatus 50 can be a mobile phone (also including a smartphone), a tablet, a mobile PC, or the like. Although not illustrated, the terminal apparatus 50 can include a control unit that performs entire control and a storage unit, and the control unit can be achieved by, for example, a CPU, a working memory, a storage apparatus, or the like, similarly to the control unit 41. In addition, a program stored in the storage apparatus can be a program for causing the CPU to achieve a function of the terminal apparatus 50.

Next, a detailed example of the information processing apparatus 10 will be described. For example, the information processing apparatus 10 can be configured by two apparatuses as illustrated in FIGS. 2 and 3. More specifically, the information processing apparatus 10 can include, as a housing thereof, two boxes such as, for example, a first external box 13 and a second external box 11. In addition, the information processing apparatus 10 can include an inter-box connection unit (inter-box connection structure) 12 that connects the first external box 13 and the second external box 11. The information processing apparatus 10 in this example can be installed on the body 21 of the toilet bowl 20 as follows, for example. In other words, the information processing apparatus 10 can be installed on the toilet bowl 20 by placing the inter-box connection unit 12 on an edge portion of the body 21 in such a way that the first external box 13 is disposed on an inside of the body 21 (on a side where an excretion range of excrement is located) and the second external box 11 is disposed on an outside of the body 21. In addition, since the information processing apparatus 10 includes various sensors installed in the toilet, it can also be referred to as a "toilet sensor" or a "toilet sensor apparatus". The toilet sensor corresponds to a so-called edge in the present system in which monitoring of toilet use by a care recipient is performed via a communication network.

The first external box 13 can accommodate, for example, the range sensor 16a that functions as a sitting sensor detecting for sitting on the toilet seat 22, and the first camera 16b capturing an image of excrement. The second external box 11 can accommodate, for example, a CPU 11a, a connector 11b, USB I/Fs 11c and 11d, a WiFi module 14a, a Bluetooth module 14b, a human detecting sensor 15a, and the second camera 15b. Note that, USB is an abbreviation for universal serial bus, and USB, WiFi, and Bluetooth are all registered trademarks (the same applies hereinafter).

Note that, the second external box 11 may not be provided with various I/Fs or connectors, and may also be directly connected to the CPU 11a. In addition, the information processing apparatus 10 may not be provided with the CPU 11a, and may only include sensors for acquiring various pieces of data, cameras, and the like, and a function of transmitting various pieces of data to a server 40 side.

As illustrated in FIG. 3, the first external box 13 and the second external box 11 are connected by an interface exemplified by the connector 11b and USB I/F 11c, and configures one information processing apparatus 10 by providing the connection line inside the inter-box connection unit 12.

The first external box 13 will be described.

The range sensor 16a is a sensor that measures a distance to an object (buttocks of a user of the toilet bowl 20) and detects that a user is sitting on the toilet seat 22, and detects that the object is sitting on the toilet seat 22 when a certain period of time has elapsed beyond a threshold value. In addition, when there is a change in the distance to the object after sitting, the range sensor 16a detects that a user has left the toilet seat 22.

As the range sensor 16a, for example, an infrared sensor, an ultrasonic sensor, an optical sensor, and the like can be adopted. When an optical sensor is adopted as the range sensor 16a, a transmission/reception element may be arranged in such a way that light (not limited to visible light) can be transmitted/received from a hole provided in the first external box 13. In the transmission/reception element herein, a transmission element and a reception element may be configured separately, or may be integrated. The range sensor 16a is connected to the CPU 11a via the connector 11b, and can transmit a detection result to a CPU 11a side. Based on the detection result, the CPU 11a can acquire leaving/sitting data indicating leaving/sitting information of a person, and can transmit the acquired data to the server 40 side via the WiFi module 14a.

The first camera 16b is one example of a camera that captures image data being a source of acquisition of the excretion information in the acquisition unit 1a in FIG. 1, and can be an optical camera whose lens portion is disposed in a hole provided in the first external box 13. As described in the first example embodiment, the first camera 16b is installed in such a way as to include, in an image capture range, an excretion range of excrement in the toilet bowl 20 of the toilet. The first camera 16b is connected to the CPU 11a via the USB I/F 11c, and transmits the captured imaging data to the CPU 11a side.

The second external box 11 will be described.

The CPU 11a is an example of a main control unit of the information processing apparatus 10, and controls the entire information processing apparatus 10. The connector 11b connects the human detecting sensor 15a and the range sensor 16a, with the CPU 11a. The USB I/F 11c connects the first camera 16b with the CPU 11a, and the USB I/F 11d connects the second camera 15b with the CPU 11a.

The human detecting sensor 15a is a sensor that detects presence of a person (entry/exit of a person) in a specific area (a measurement area range of the human detecting sensor 15a) being a part of a room of the toilet, and can be referred to as an entry/exit sensor. As the human detecting sensor 15a, for example, an infrared sensor, an ultrasonic sensor, an optical sensor, and the like can be adopted regardless of the detection method. The human detecting sensor 15a is connected to the CPU 11a via the connector 11b, and transmits a detection result to the CPU 11a when a person is detected in the specific area. The detection result can be transmitted by the CPU 11a to the server 40 via the WiFi module 14a.

The second camera 15b can be an optical camera whose lens portion is disposed in a hole provided in the second external box 11, and is an example of a camera that captures a face image of a user of the toilet and acquires face image data in order to identify the user. The second camera 15b can be installed on the toilet bowl 20 in such a way as to include a face of a user in an image capture range, but can also be installed in the room of the toilet where the toilet bowl 20 is installed. As described above, the second camera 15b can also be used as a part of the authentication unit 1d in FIG. 1, and authentication of a person can be performed by performing face authentication processing by using face image data captured by the second camera 15b. Note that, in the present system, when the human detecting sensor 15a detects a person, processing can be performed such that the second camera 15b captures an image of a subject who has entered the toilet. Thus, the face authentication can be performed only when a person is detected.

The Bluetooth module 14b is one example of a receiver that receives identification data for identifying a user from a Bluetooth tag held by the user, and can also be replaced with a module based on another near-field communication standard. The Bluetooth tag held by a user can be set as a different ID for each user, and held by the user, for example, by being embedded in a wristband and the like. As described above, the Bluetooth module 14b can be used as a part of the authentication unit 1d in FIG. 1, and can authenticate a person based on the received identification data. As described above, in the configuration example in FIG. 3, two of the second camera 15b and the Bluetooth module 14b are provided as a function of acquiring information for human authentication.

The WiFi module 14a is one example of a communication apparatus that transmits various pieces of acquired data to the server 40, and can be replaced with a module adopting another communication standard. Face image data acquired by the second camera 15b and identification data acquired by the Bluetooth module 14b can be transmitted by the CPU 11a to the server 40 via the WiFi module 14a.

The CPU 11a, the USB I/F 11c, the WiFi module 14a, and the server 40 can be one example of the acquisition unit 1a in FIG. 1, and acquires excretion information, based on the imaging data captured by the first camera 16b. In this case, the server 40 can be responsible for main processing of acquiring the excretion information from the imaging data. The server 40 in the example in FIG. 2 inputs the imaging data into a learned model, for example, and acquires the excretion information. Then, the server 40 preferably mainly acquires, as a part of pieces of the excretion information, information indicating whether a foreign body being an object other than feces and urine is included in the imaging data as a subject excluding the toilet bowl and washing liquid for the toilet bowl. The foreign body can also be referred to as another object, may be liquid or solid as long as other than faces and urine, and can include, for example, any one or plural of vomit, melena, vomiting of blood (hematemesis), a diaper, a urine absorbing pad, a toilet paper core, and the like. In addition, the server 40 can be configured to acquire a shape, color, and amount of excrement as the excretion information when there is not a foreign body but excrement.

The CPU 11a, the WiFi module 14a, the server 40, and the terminal apparatus 50 can be one example of the output unit 1f in FIG. 1. In this case, the server 40 can be responsible for main processing of detecting, from excretion information, entry/exit information, leaving/sitting information, and an authentication result, a detection event indicated by the excretion information, the entry/exit information, the leaving/sitting information, and the authentication result. In addition, in this case, the terminal apparatus 50 can be responsible for main processing of outputting notification information, and the terminal apparatus 50 receives the notification information transmitted from the server 40, and notifies the received notification information by display and/or audio output.

In addition, the server 40 can store information such as excretion information, entry/exit information, leaving/sitting information, and an authentication result in the storage unit 42 or the like, and output the information in response to access from the terminal apparatus 50, for example. In particular, it is desirable that the server 40 has a function of generating an excretion diary, and in that case, by storing the generated excretion diary in the storage unit 42, the excretion diary can be viewed from the terminal apparatus 50 when a caregiver being a user of the terminal apparatus 50 desires. Note that, although the excretion diary includes a date and time of excretion behavior, the date and time can be acquired by any one of an imaging date and time of the imaging data, an identification date and time of a subject, an entry/exit date and time, a sitting date and time, a leaving date and time, a date and time in a middle of the sitting and leaving, and the like.

The server 40 receives the face image data acquired by the second camera 15b via the WiFi module 14a, performs face authentication processing by comparing authentication data stored in advance with, for example, a feature point thereof and the like, and acquires identification data associated with matched authentication data. In this way, the server 40 can acquire identification data (identification data for identifying a user), that is, specify a user.

Then, the server 40 can acquire, from the information processing apparatus 10 together with imaging data, face image data of a user (a person to be assisted) of the toilet bowl 20 or a helper at a time of acquiring the imaging data. Therefore, the control unit 41 of the server 40 can identify a person who has entered, based on the face image data, and can determine whether to be matched with the notification condition stored in the storage unit 42 by using identification information of the person as a key. Note that, it is preferred not to store the face image data captured by the second camera 15b, in consideration of privacy.

Further, the server 40 receives identification data (personal authentication data) acquired by the Bluetooth module 14b via the WiFi module 14a, and performs user authentication by comparing with authentication identification data stored in advance. Note that, for example, even when a caregiver holding his/her Bluetooth tag and a care receiver holding his/her Bluetooth tag enter a toilet together, the both can be distinguished and recognized with each other. In this way, the server 40 can acquire identification data of a person who has entered the toilet. Then, the control unit 41 of the server 40 can determine whether to be matched with the notification condition stored in the storage unit 42 by using the identification data as a key.

Note that, in the example, it can be said that a person to be assisted and a helper are specified from two types of data, i.e., face image data and identification data, and two specification functions are provided, but of course, a person to be assisted and a helper can be specified by either one. For example, the present system provides both specification functions, and can select one of them at a time of operation. Alternatively, the present system can provide only one of the specification functions.

As described above, a detection result by the human detecting sensor 15a can be transmitted to the server 40. Since the detection result can be used for determining entry/exit to/from the toilet, even when there is no detection, the server 40 can acquire the information. When the detection result is received from the information processing apparatus 10, the server 40 stores, in the storage unit 42 and the like, data (entry/exit data) indicating entry/exit to/from the toilet being an installation location of the toilet bowl 20 in association with the identification data of the specified user as described above. Note that, the entry/exit data can also include the identification data.

Then, the control unit 41 of the server 40 compares an authentication result of a person indicated by the received identification data, entry/exit information indicated by the entry/exit data, leaving/sitting information indicated by the leaving/sitting data, and excretion information indicating a start and end of excretion with the notification condition stored in the storage unit 42. As a result of this comparison, when there is a matched notification condition, the control unit 41 outputs notification information indicated by the notification condition to a notification destination indicated by the notification condition.

The notification destination can be the terminal apparatus 50 held by any one or a plurality of helpers, and which helper is the notification destination is included in the notification condition. Note that, the notification destination may be, for example, a notification apparatus of a nurse call system, another terminal apparatus (for example, a personal handy-phone system (PHS)) possessed by a caregiver other than the terminal apparatus 50, an intercom, or the like, in addition to or in place of the terminal apparatus 50.

In addition, the notification condition preferably includes importance information indicating importance of notification. In this case, the control unit 41 of the server 40 can transmit notification information to the notification destination in a state including the importance information, or can transmit the notification information to the notification destination in a state indicating the importance information. As a result, it is possible to detect, with respect to toilet use by a care recipient, entry to the toilet, sitting on the toilet seat 22, a start of excretion, an end of excretion, leaving from the toilet seat 22, and exit from the toilet, and to notify the caregiver who becomes a helper according to presence or absence of notification and the importance which set for each care recipient for detection event. In addition, when the importance information is included in the notification condition, it is also possible to determine necessity of the notification according to the importance. In addition, the notification condition includes notification information indicating a notification content in addition to the necessity (presence or absence) of notification and the importance, and notification is performed on the detection event, based on such a notification condition.

In addition, the detection event preferably includes a first event being an event in which a person to be assisted as a user sits on the toilet seat 22 for a certain period of time (for example, a long period of time such as 10 minutes) or more. The first event is equivalent to an abnormal event in which a care recipient needs assistance. Thus, as a notification condition for the first event, the notification destination includes a contact address of a helper who assists the person to be assisted as a user, and the notification information includes an alert requesting assistance. One or a plurality of caregivers may be determined in advance as a helper for the person to be assisted. In addition, the alert also includes information specifying a location of the toilet.

In addition, the detection event preferably includes a second event being an event in which a foreign body is detected in imaging data. The second event is equivalent to an abnormal event that requires cleaning of the toilet. Thus, as a notification condition for the second event, the notification destination includes a contact address of a helper who assists a person to be assisted as a user, and the notification information includes an alert requesting removal of a foreign body. The alert also includes information specifying a location of the toilet. In this case, the notification destination may include a contact address of a cleaner, but by including the contact address of the helper as described above, it is possible to recognize behavior such as insertion of a diaper or the like into the toilet bowl 22 by a person to be assisted.

In addition, the detection event preferably includes a third event being an event in which at least one of the first camera 16b, the first sensor (the human detecting sensor 15a and/or the second camera 15b), and the range sensor 16a detects dirt. The third event is an abnormal event requiring cleaning as maintenance of the present system. Thus, as a notification condition for the third event, the notification destination includes a contact address of a person who can become a helper, and the notification information includes an alert requesting removal of the dirt described above. The alert also includes information specifying a location of the toilet. In this case, the notification destination may include a contact address of a maintenance contractor or a contact address of a cleaner, but by including the contact address of the helper as described above, it is possible to recognize dirty behavior by a person to be assisted.

In addition, the detection event preferably includes a fourth event being an event in which it is detected that a helper enters a toilet while a person to be assisted as a user enters the toilet. The fourth event is a notification event indicating that the person to be assisted is being assisted by the helper. Thus, as a notification condition for the fourth event, the notification destination includes a contact address of a person who can become a helper other than the helper according to the fourth event, and the notification information includes information notifying that a person to be assisted as a user is being assisted. Then, when the fourth event occurs, another detection event not being notified until at least a state indicated by the fourth event disappears can be included. An event (another specific detection event) not being notified at a time of the fourth event can be an event that requires a helper. On the other hand, in a case of a notification event that can be handled by, for example, a cleaner or a maintenance person, the notification may be performed without being included in the another specific detection event described above.

In addition, the server 40 preferably includes a reception unit (not illustrated) that receives, from a person who can become a helper, rush information that notifies a person who can become another helper to rush in order to assist a person to be assisted. In this case, the detection event preferably includes a fifth event indicating that the rush information is received by the reception unit described above. The fifth event is a notification event indicating during rushing. Thus, as a notification condition for the fifth event, the notification destination includes a contact address of a person who can become another helper, and the notification information includes information notifying to rush in order to assist a person to be assisted. The alert also includes information specifying a location of the toilet. With such a rush notification, it is possible to prevent waste of rushing, by a caregiver, to the toilet of the same care recipient.

In addition, the reception unit can be configured in such a way as to receive rush stop information notifying that rushing cannot be made from a transmission destination of the rush information. In this case, the detection event preferably includes a sixth event indicating that the reception unit has received the rush stop information. The sixth event is a notification event indicating that rushing is planned but stopped. Thus, as a notification condition for the sixth event, the notification destination is the same as the notification destination for the fifth event, and the notification information includes information indicating that rushing for assistance of a person to be assisted has been stopped. The alert also includes information specifying a location of the toilet. With such a rush stop notification, it is possible to prevent a care recipient from being left unattended when the caregiver cannot rush to the toilet of the care recipient after the rush notification.

In addition, the server 40 may include a setting unit (not illustrated) that sets a notification condition from the terminal apparatus 50 or the like. The setting unit can be mounted as a part of the function of the control unit 41, accepts a change operation such as addition, correction, or deletion of a notification condition from the terminal apparatus 50 or the like, and changes the notification condition stored in the storage unit 42 according to the change operation.

Figure 4:
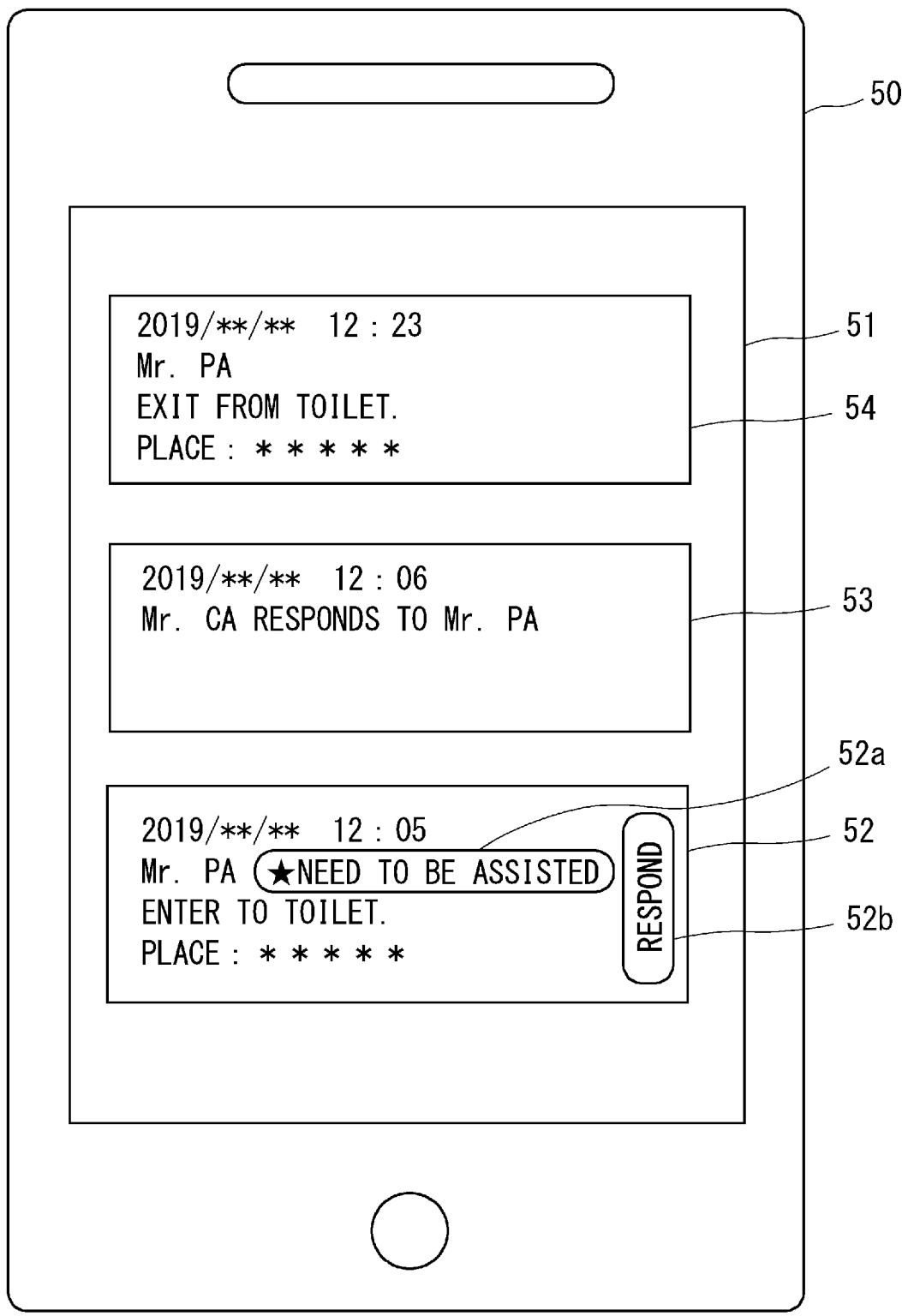
FIG. 4 is a diagram for describing a notification example in a terminal apparatus in the information processing system in FIG. 2.

Next, a display example of notification information to the terminal apparatus 50 will be described with reference to FIG. 4. FIG. 4 is a diagram for describing a notification example in the terminal apparatus in the information processing system in FIG. 2.

As illustrated in FIG. 4, the terminal apparatus 50 can notify notification information 52 to 54 in a timely manner on a display screen 51 of the terminal apparatus 50. The notification information 52 is an example of information that, when a person is detected by the human detecting sensor 15a, identifies a user (in this example, a care recipient PA) and notifies entry of the user to a toilet. Identification of a user can be acquired as a result of performing face authentication processing based on face image data acquired by the second camera 15b or identification processing received by the Bluetooth module 14b when a person is detected by the human detecting sensor 15a. By recording a care receiver who needs care with a plurality of persons in a face authentication person list or an identification person list, when a detected person is the person, the notification information 52 can include information notifying that the person is a subject who needs care with a plurality of persons next to a name (Mr. PA in this example). In addition, it is desirable to add information 52a including a mark (herein, a star mark) indicating importance to the notification information 52, and the notification information 52 can also include a button 52b for selecting to notify that the user handles the care receiver.

When a caregiver CA selects the button 52b in the terminal apparatus 50 and the server 40 receives the selection at the reception unit, the present system can be configured to display the notification information 53 on the terminal apparatus 50 of another caregiver (and the terminal apparatus 50 of the caregiver CA), for example. The notification information 53 can include information indicating that Mr. CA handles Mr. PA, and is notification information associated to the fifth event. In particular, in a case where a person is a subject who needs care with a plurality of persons as in the example of Mr. PA, when the button 52b is selected, the present system can also be configured to notify the terminal apparatus 50 used by a person who can become another helper of a request to handle the care receiver. In addition, the notification information 54 is an example of information for notifying exit from the toilet when a detection state is changed to a non-detection state for Mr. PA.

Figure 5:
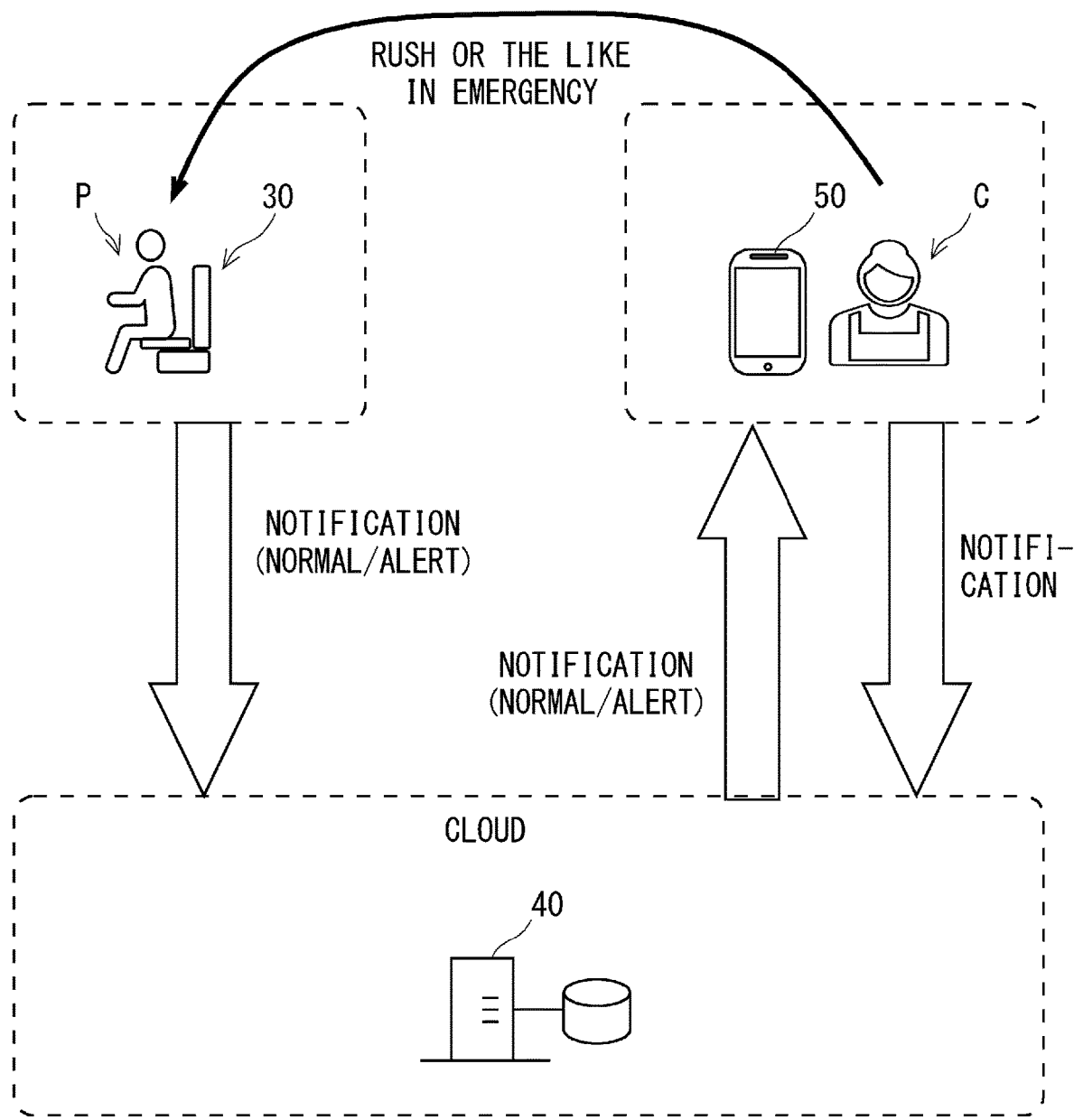
FIG. 5 is a schematic diagram for describing a flow of notification in the information processing system in FIG. 2.
Figure 9:
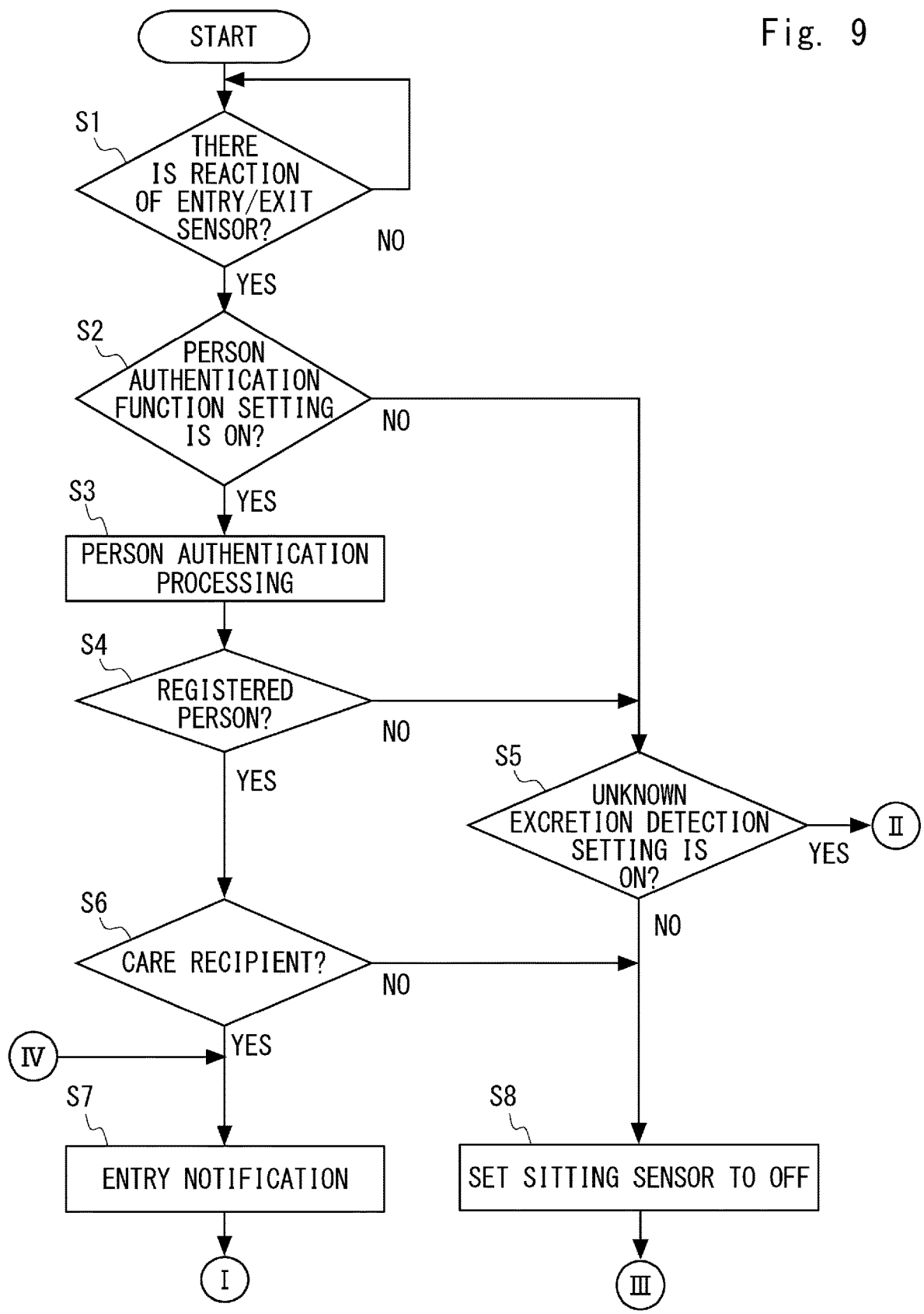
FIG. 9 is a flowchart for describing one example of notification processing in the information processing system in FIG. 2.
Figure 10:
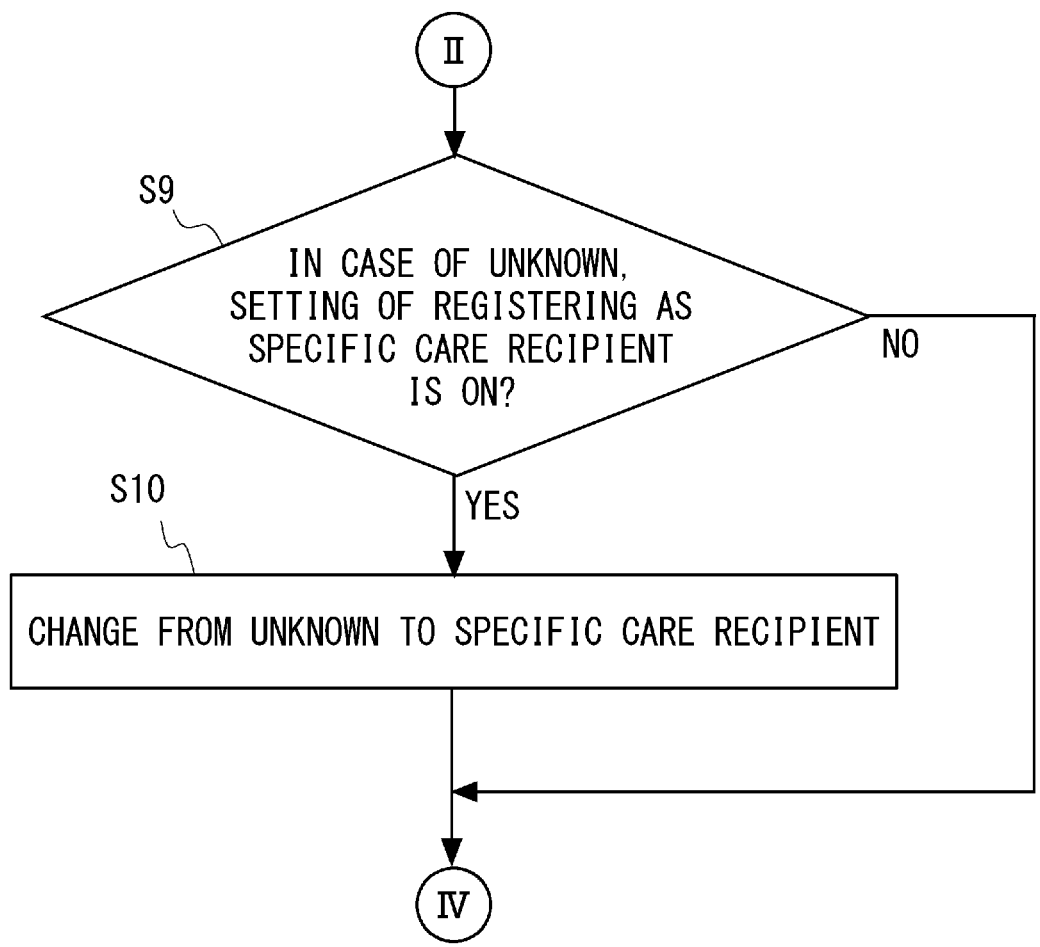
FIG. 10 is a flowchart following FIG. 9.
Figure 11:
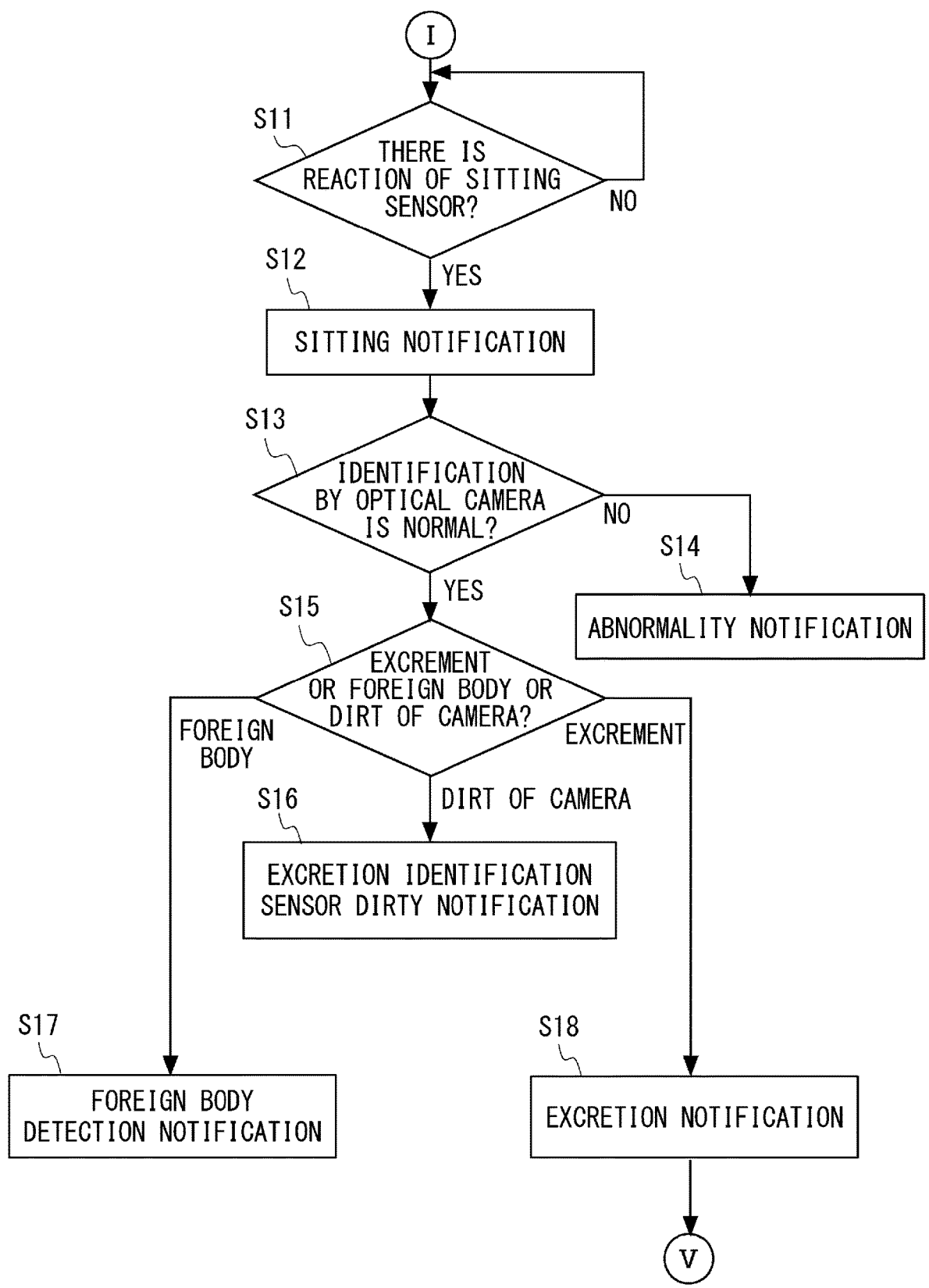
FIG. 11 is a flowchart following FIG. 9.
Figure 12:
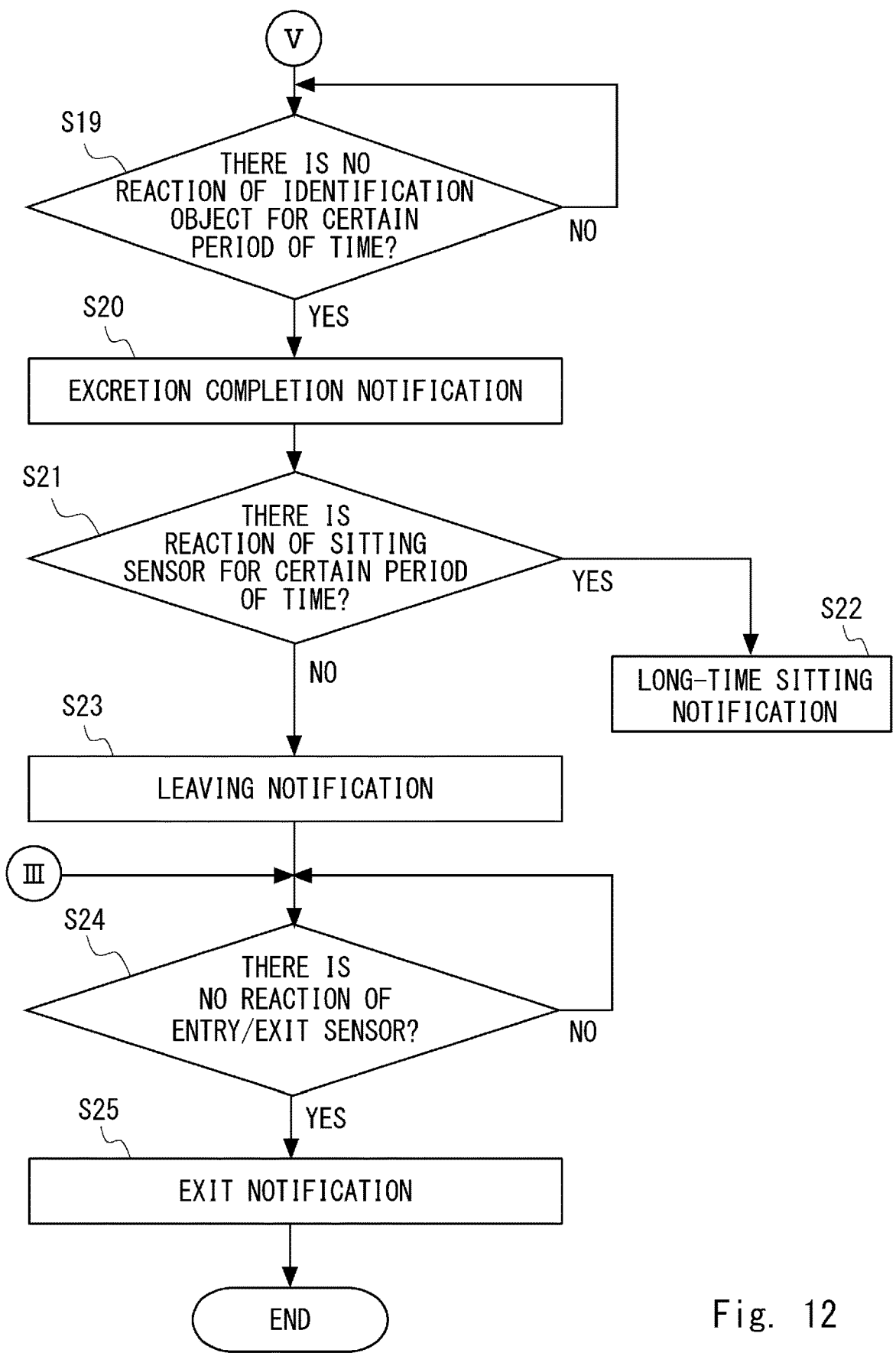
FIG. 12 is a flowchart following FIG. 11.

Next, a more specific example of a notification condition and notification processing based on the notification condition will be described with reference to FIGS. 5 to 8. FIG. 5 is a schematic diagram for describing a flow of notification in the information processing system in FIG. 2. FIG. 6 is a diagram illustrating an example of a notification condition in the information processing system in FIG. 2, FIG. 7 is a diagram illustrating an example of a notification type and a setting content in the notification condition in FIG. 6, and FIG. 8 is a diagram illustrating a purpose of the notification type in FIG. 7.

As illustrated in FIG. 5, the toilet bowl 30 with the information processing apparatus (toilet sensor) 10 transmits, when detecting that a person has entered a toilet by the human detecting sensor 15a and/or the second camera 15b that are caused to function as an entry/exit sensor, an entry notification and information acquired by the entry/exit sensor to the server 40. The server 40 receives the entry notification and the information, executes person authentication processing, specifies a person who entered, and transmits the entry notification to the terminal apparatus 50 such as a smartphone of a caregiver C who is located at a place away from the toilet.

In addition, when the toilet sensor 10 detects that a user sits on the toilet seat 22 of the toilet by the range sensor 16a being caused to function as a sitting sensor, the toilet sensor 10 transmits a sitting notification to the server 40, and also starts imaging by the first camera 16b and transmits imaging data to the server 40. When receiving the sitting notification, the server 40 determines that the user is a care recipient from the information acquired by the entry/exit sensor, also analyzes the received imaging data, and transmits an excretion start notification to the terminal apparatus 50 of the caregiver C when a start of excretion is detected.

In addition, when completion of excretion is detected from the imaging data, the server 40 transmits an excretion end notification to the terminal apparatus 50 of the caregiver C. The toilet sensor 10 transmits a leaving notification to the server 40 at a time of leaving the seat and an exit notification to the server 40 at a time of exit, based on a detection result by the sitting sensor and the entry/exit sensor. When receiving the leaving notification or the exit notification, the server 40 transmits the received notification to the terminal apparatus 50 of the caregiver C. As a result, the caregiver C is released from constant attendance status at a time of excretion of a care recipient, and can rush or the like in an emergency (for example, in a case where there is no leaving notification for long time) as necessary. The caregiver C confirms notification by the terminal apparatus 50, transmits the rush notification from the terminal apparatus 50 to the server 40 in case of performing assistance, and performs rush. When the caregiver C is unable to rush, the caregiver C operates the terminal apparatus 50 and transmits the rush stop notification to the server 40. The server 40 transfers the received rush stop notification to another caregiver.

The notification processing as illustrated in FIG. 5 can be executed with reference to a notification condition illustrated in FIG. 6. As illustrated in FIG. 6, in notification related to the toilet use, there is notification that presence or absence of notification (necessity of notification) is different depending on an assistance state of a care recipient, and the presence or absence of the notification can be determined by an assistance-in-progress notification filter. The assistance-in-progress notification filter is equivalent to a filter for determining whether an event is the another specific detection event described above at a time of detection of the fourth event described above. In the present system, when a caregiver is present in a toilet being used by a care recipient, it is determined that the assistance state of the care recipient is assistance in progress, and when the caregiver is not present, it is determined that the assistance state is non-assistance. When performing notification, the assistance-in-progress notification filter confirms the assistance state of the care recipient, stops the notification to the caregiver in a case of assistance in progress, and continues the notification to the caregiver in a case of non-assistance.

Since notifications of Nos. 1 to 7 and 11 to 14 in FIG. 6 are a target of the assistance-in-progress notification filter, the presence or absence of the notification differs depending on presence or absence of the caregiver. Notifications of Nos. 8 to 10 are performed in order to notify a caregiver or the like of a state of the toilet sensor 10 (a foreign body detection state, a dirty state, and a service recovery state), and therefore are not a target of the assistance-in-progress notification filter. Thus, the notification is performed regardless of the assistance state of the care recipient.

The notification type and setting content of the notification related to the toilet use will be described with reference to FIGS. 7 and 8. Since necessity of assistance differs for each care recipient, the notification condition may be set such that importance of each notification is also different for each care recipient. Therefore, classification of "alert notification", "normal notification", and "not notified" illustrated in FIG. 8 is defined as the notification type, and can be individually set according to a state of the care recipient.

Notifications of Nos. 1 to 6 set the notification type for each care recipient, set alert notification for the notification type when assistance by a caregiver is required, and set normal notification for the notification type when assistance by a caregiver is not required. As described above, the notification condition can be set for each person to be assisted as a user. With regard to a notification of No. 7, since there is a high possibility that abnormality has occurred in a care recipient, the alert notification is set in the notification type. In addition, with regard to notifications of Nos. 8 and 9, since abnormality has occurred in the toilet sensor, the alert notification is set in the notification type. The settings for Nos. 7 to 9 are fixed. Notifications of Nos. 10 to 14 are fixed to the normal notification.

Next, an example of the notification processing in the present system will be described. Processing in the toilet sensor 10 is mainly executed by the CPU 11a, and processing in the server 40 is mainly executed by the control unit 41.

First, an example of notification processing triggered by entry of a care recipient to a toilet will be described as a more specific example of notification processing based on a notification condition with reference to FIGS. 9 to 12. Note that, herein, a case where a user of the toilet becomes a person to be assisted (i.e., a person required to be assisted) will be described. FIGS. 9 to 12 are a series of flowcharts for describing one example of the notification processing in the information processing system in FIG. 2. Note that, various pieces of notification to be performed below are performed to the terminal apparatus 50 of a contact address described in the notification condition, for example, a contact address of a caregiver who is in charge of a care recipient, or the like.

First, the toilet sensor 10 checks presence or absence of a reaction of an entry/exit sensor (step S1). When a user enters the toilet, the entry/exit sensor reacts, and YES is acquired in step S1. When there is no reaction, processing waits until there is a reaction (until becoming YES).

When YES in step S1, the toilet sensor 10 determines whether a person authentication function setting is ON (step S2). When YES in step S2, the toilet sensor 10 cooperates with the server 40 and performs person authentication processing (step S3), determines whether to be a registered person (step S4), and determines whether to be a care recipient when being the registered person (step S6). When NO in step S2 (when the person authentication function setting is OFF), the processing proceeds to step S5. When NO in step S4 (when a person authentication result is a non-registered person), the processing also proceeds to step S5.

When YES in step S6, that is, when it is determined from the person authentication result that the person is a care recipient, the server 40 performs, on the terminal apparatus 50, a toilet entry notification indicating that the care recipient has entered the toilet (step S7). The notification destination can be a contact address of a caregiver stored as a notification condition. On the other hand, when NO in step S6, that is, when it is determined from the person authentication result that the person is not the care recipient, the server 40 causes the toilet sensor 10 to set the sitting sensor to OFF (step S8), and the processing waits until the person who has entered exits (proceeds to step S24 to be described later). As described as step S2 and the subsequent processing, the present system can be configured to be settable execution/non-execution of the person authentication processing.

In step S5, the server 40 determines whether an unknown excretion detection setting is ON. The setting is a setting indicating whether to acquire excretion information for an unknown user. When NO in step S5, that is, when the unknown excretion detection setting is OFF, the server 40 proceeds to step S8 and causes the toilet sensor 10 to set the sitting sensor to OFF, and the processing waits until the person who entered exits (proceeds to step S24 to be described later). In this way, the present system can be configured to be settable whether to acquire excretion information for an unknown user.

When YES in step S5, the server 40 determines whether a setting of registering as a specific care recipient is ON when the person authentication result is unknown (step S9). The setting is a setting indicating whether notification processing is performed by handling as a registered specific care recipient with the specific care recipient as described above as a result or notification processing is performed by handling the registered specific care recipient with unknown, even in a scene where the registered specific care recipient is determined to be unknown. When YES in step S9, the server 40 changes the entry person from unknown to a specific care recipient (step S10), the processing proceeds to step S7, and performs the toilet entry notification. On the other hand, when NO in step S9, that is, when the person authentication result is unknown in a case where the setting of registering as a specific care recipient is OFF, the server 40 proceeds to step S7 while keeping the entry person as unknown, and performs the toilet entry notification.

After the toilet entry notification is performed in step S7, the toilet sensor 10 determines whether there is a reaction of the sitting sensor (step S11), and the processing waits until there is a reaction. When YES in step S11 (when there is a reaction of the sitting sensor), the toilet sensor 10 transmits a sitting notification to the server 40, and the server 40 that has received the transmitted notification performs the sitting notification to the terminal apparatus 50 (step S12).

Next, the toilet sensor 10 captures an image in the toilet bowl by an optical camera and transmits imaging data to the server 40 (step S13), and the server 40 determines whether there is an object whose imaging data is normally identifiable (image detectable) (step S13). When NO in step S13 (when abnormality is detected, for example, when no subject is reflected, and the like), the server 40 performs an abnormality notification to the terminal apparatus 50 because there is a possibility that some abnormality has occurred in the care recipient in the toilet (step S14). When YES in step S13 (in a case of a state where identification can be performed normally), the server 40 performs an image analysis of the imaging data, and determines (identifies or classifies) whether the object to be detected is equivalent to any one of excrement, a foreign body, and dirt of a camera or the like (step S15).

When the dirt of the camera or the like is detected in step S15, the server 40 performs a notification for the dirt of an excretion identification sensor on the terminal apparatus 50 (step S16). When the foreign body is detected in step S15, the server 40 performs a notification for detection of the foreign body in the toilet bowl on the terminal apparatus 50 (step S17). When excrement is detected in step S15, the server 40 performs an excretion start notification indicating that the care recipient has started excretion on the terminal apparatus 50 (step S18).

Subsequently to step S18, the server 40 determines whether an identification object (excrement or foreign body) has not been detected for a certain period of time, based on the imaging data to be transmitted from the toilet sensor 10 (step S19). When there is no reaction (YES in step S19), the server 40 performs an excretion completion notification indicating that the care recipient has completed excretion on the terminal apparatus 50 (step S20). When NO in step S19 (when the reaction continues), the server 40 waits until YES in step S19.

Subsequently to step S20, the server 40 determines whether there is a reaction of the sitting sensor transmitted from the toilet sensor 10 for a certain period of time (step S21). When a state where there is a reaction has elapsed for a certain period of time (YES in step S21), there is a possibility that some abnormality has occurred in the care recipient because the care recipient is sitting for a long time. Therefore, in this case, the server 40 performs a notification for long-time sitting on the terminal apparatus 50 (step S22). When there is no reaction of the sitting sensor for a certain period of time (NO in step S21), the server 40 performs a notification of leaving (i.e., standing up) on the terminal apparatus 50 (step S23).

Subsequently to step S23, the server 40 determines whether there is a reaction of the entry/exit sensor (step S24), and waits until becoming YES (until no reaction). When there is no reaction of the entry/exit sensor, the server 40 performs a toilet exit notification on the terminal apparatus 50 (step S25), and ends the processing.

Figure 13:
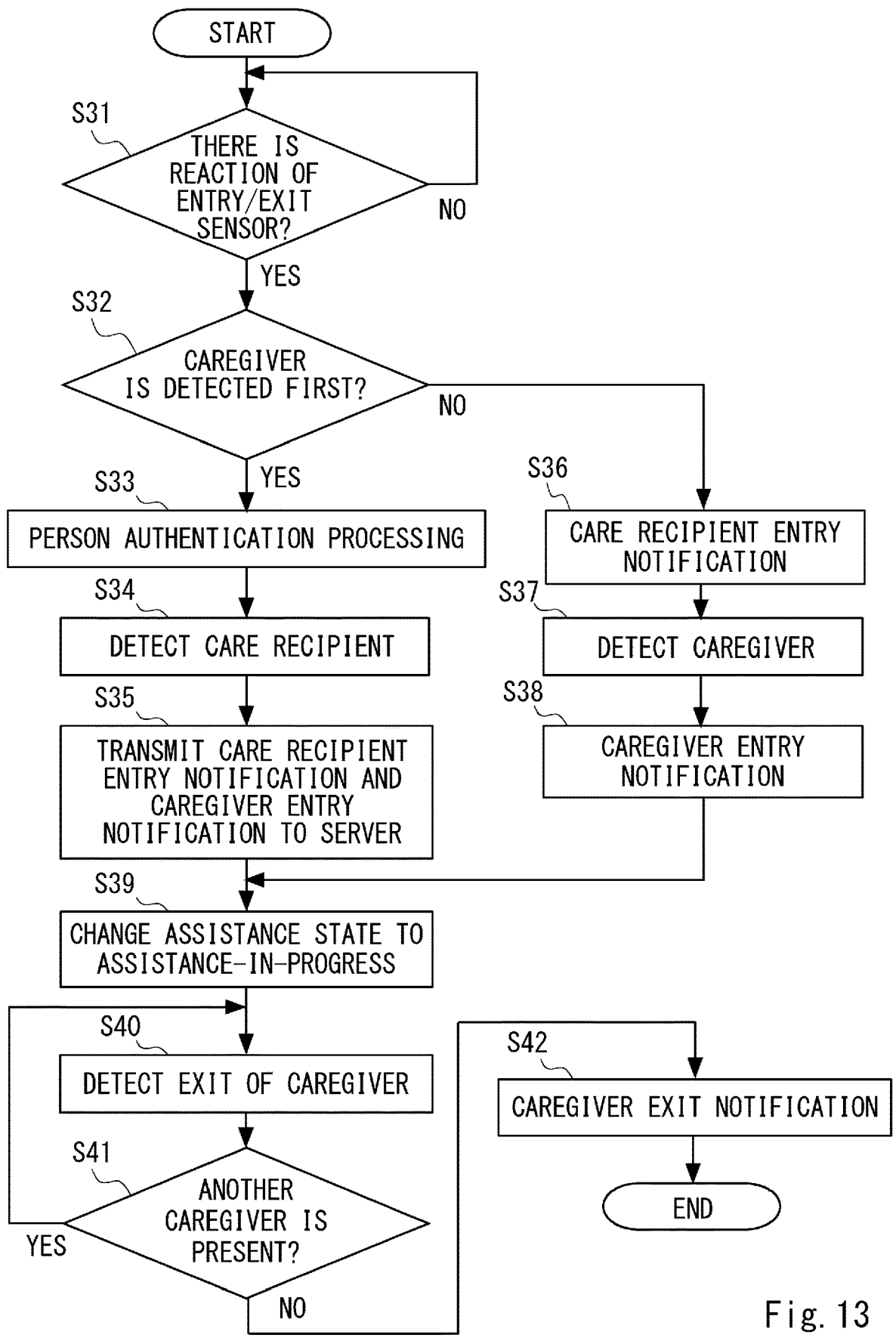
FIG. 13 is a flowchart for describing another example of the notification processing in the information processing system in FIG. 2.

FIG. 13 is a flowchart for describing another example of the notification processing in the information processing system in FIG. 2, and is a flowchart for describing one example of the notification processing triggered by entry of a caregiver to a toilet with a care recipient.

First, the toilet sensor 10 checks presence or absence of a reaction of an entry/exit sensor (step S31). When a person enters the toilet, the entry/exit sensor reacts, and YES is acquired in step S31. When there is no reaction, processing waits until there is a reaction (until becoming YES). When YES in step S31, the toilet sensor 10 cooperates with the server 40 and determines whether to be a caregiver (i.e., whether the caregiver has been detected first) (step S32). However, herein, an example in which only the caregiver can be detected by the Bluetooth module 14b is described.

When YES in step S32, a caregiver entry notification is not performed, and the toilet sensor 10 cooperates with the server 40 and performs the person authentication processing (step S33), and detects a care recipient (step S34). Next, the toilet sensor 10 transmits a care recipient entry notification and the caregiver entry notification to the server 40 (step S35). However, herein, the server 40 does not perform the notification on the caregiver (does not notify the terminal apparatus 50).

When NO in step S32 (when the care recipient is detected first), the server 40 performs the care recipient entry notification indicating that the care recipient has entered on the terminal apparatus 50 (step S36). Next, the toilet sensor 10 cooperates with the server 40 and detects a caregiver (step S37), and thereafter performs the caregiver entry notification indicating that the caregiver has entered on the terminal apparatus 50 (the terminal apparatus 50 used by another caregiver) (step S38).

After the processing in step S35 and after the processing in step S38, since the caregiver is entering, the server 40 changes an assistance state to assistance in progress (step S39). Next, after the caregiver assists the care recipient in the toilet, the server 40 detects exit of the caregiver, based on a detection result of the entry/exit sensor (step S40). Thereafter, the server 40 determines whether another caregiver is still present, based on the detection result of the entry/exit sensor (step S41), and when the caregiver is present on a seat, since the assistance state remains in assistance in progress, the notification is not performed, and the processing returns to step S40. When NO in step S41 (when all the caregivers exit), since the assistance state is other than assistance in progress, the server 40 performs the caregiver exit notification indicating that the caregiver has exit on the terminal apparatus 50 (step S42), and the processing ends.

Figure 14:
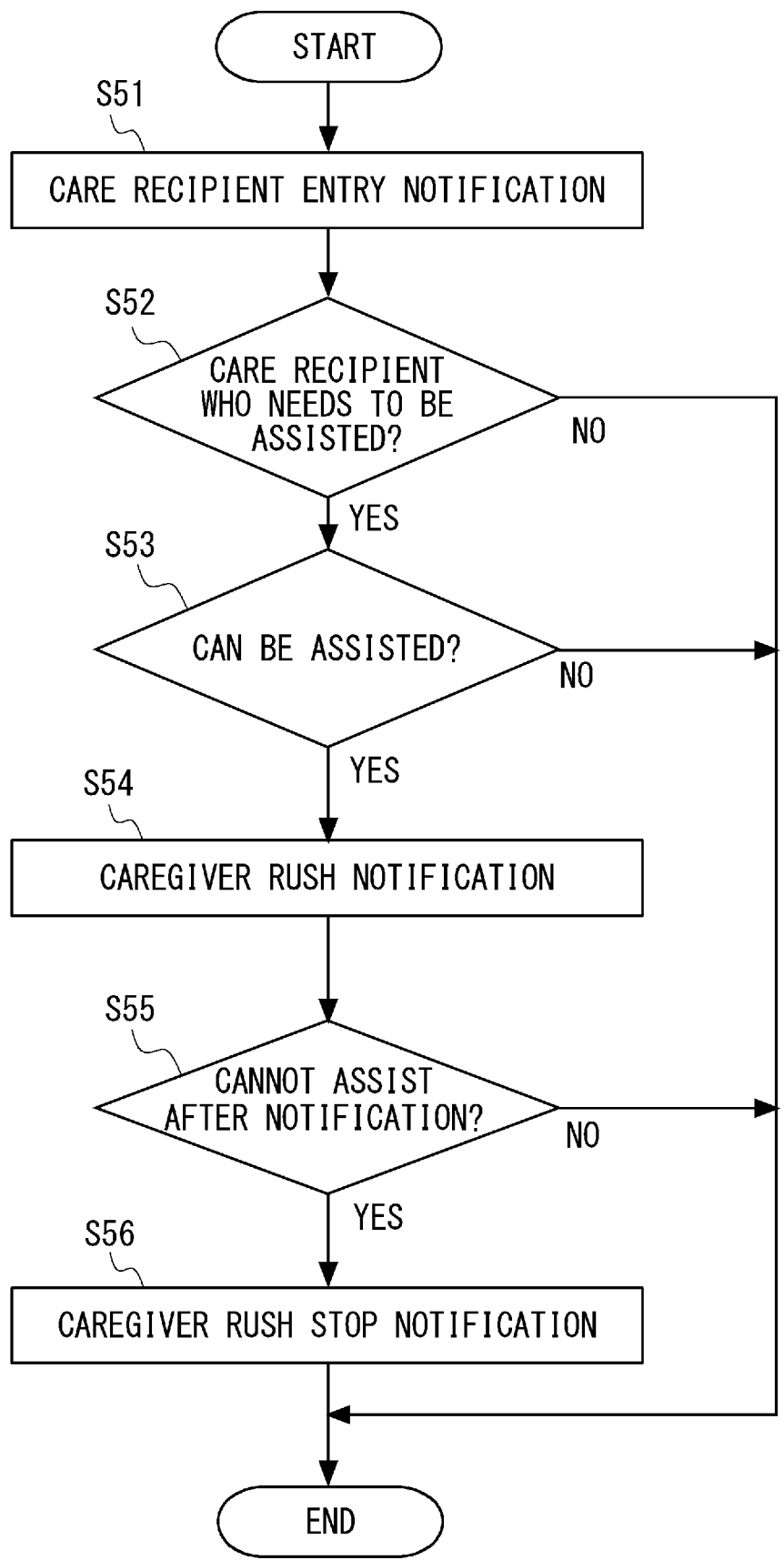
FIG. 14 is a flowchart for describing another example of the notification processing in the information processing system in FIG. 2.

FIG. 14 is a flowchart for describing another example of the notification processing in the information processing system in FIG. 2, and is a flowchart for describing one example of the notification processing triggered by a terminal operation of a caregiver. Note that, herein, a processing example will be described together with judgment and an operation of the caregiver.

The terminal apparatus 50 used by the caregiver receives a care recipient entry notification (step S51). In response to the notification, the caregiver confirms whether to be a care recipient who needs assistance (step S52). In a case of a care recipient who does not need assistance, only the notification is confirmed, and the processing ends.

On the other hand, in a case of a care recipient who needs assistance (YES in step S52), when the caregiver can assist, the caregiver operates the terminal apparatus 50 in such a way as to transmit a caregiver rush notification to the server 40, and goes to the assistance. By this operation, the caregiver rush notification is transmitted from the terminal apparatus 50 to the server 40 (step S54). When the caregiver cannot rush after the caregiver rush notification is transmitted (YES in step S55), the caregiver operates the terminal apparatus 50 in such a way as to transmit a caregiver rush stop notification to the server 40. By this operation, the caregiver rush stop notification is transmitted from the terminal apparatus 50 to the server 40. When receiving the notification, the server 40 transmits the caregiver rush stop notification to the terminal apparatus 50 of another caregiver (step S54), and ends the processing.

As described above, in the present example embodiment, processing is started by the toilet sensor 10 detecting that a person has entered a toilet. When the toilet sensor 10 or the server 40 detects entry of a person to the toilet, person authentication processing is executed for the person who enters the toilet in order to specify the person. In the toilet sensor 10 or the server 40, information on a "care recipient" and a "caregiver" is registered in advance as information to be used in the person authentication processing, and when an unregistered person enters the toilet sensor 10 or the person authentication fails, the person who enters is set to "unknown". As described above, the toilet sensor 10 or the server 40 executes the person authentication processing with reference to person information (caregiver information and care recipient information) registered in advance with respect to the person who enters the toilet, and specifies the person who enters the toilet.

When a person specified by the person authentication processing is a care recipient, the toilet sensor 10 detects entry/exit of the care recipient to/from the toilet, sitting/leaving on/from a toilet seat, and a start/end of excretion by using the entry/exit sensor, the sitting sensor, and the excretion identification sensor. When the toilet sensor 10 detects an event of the care recipient in the toilet, the toilet sensor 10 performs notification to the caregiver. Specifically, when the entry of the care recipient is detected by the person authentication processing, the toilet sensor 10 performs a toilet entry notification. After the toilet entry notification, the toilet sensor 10 performs a toilet sitting notification when detecting sitting on the toilet seat by the care recipient. After the toilet sitting notification, the toilet sensor 10 performs a toilet excretion start notification when detecting a start of excretion of the care recipient, and performs a toilet excretion end notification when detecting an end of excretion. After the excretion end notification, the toilet sensor 10 performs a toilet leaving notification when detecting leaving from the toilet seat by the care recipient. After the toilet leaving notification, the toilet sensor 10 monitors exit, and performs a toilet exit notification when detecting exit of the care recipient. In addition, when the care recipient remains sitting on the toilet seat for a long time, the toilet sensor 10 notifies the caregiver of occurrence of abnormality. In addition to the above, when a foreign body other than excrement is detected in the toilet bowl, the toilet sensor 10 notifies the caregiver of detection of the foreign body, and prevents the foreign body from flushing together with excrement.

These notifications are performed from the toilet sensor 10 to the server 40 through a network, and are finally notified to the caregiver. In addition, for these notifications, presence or absence of notification and importance ("alert notification" "normal notification") can be set for each care recipient as a notification condition, the importance is set according to a state of the care recipient, and there is a case where the notification is performed to the caregiver, or a case where the notification to the caregiver is stopped. The caregiver can recognize, by the notification, that the care recipient is using the toilet, and can determine whether to rush to assistance by the importance of the notification.

As described above, by detecting a movement of the care recipient in the toilet and raising the notification, the caregiver can confirm the entry/exit of the toilet, the sitting/leaving on the toilet seat, and the start/end of excretion without waiting near the care recipient. In addition, presence or absence of each notification differs from each other depending on the assistance state of the care recipient, and the presence or absence of the notification can be determined by an assistance-in-progress notification filter. The toilet sensor 10 confirms presence or absence of a caregiver in the toilet being used by the care recipient, and determines that the assistance state of the care recipient is assistance in progress or non-assistance. When the toilet sensor 10 performs notification, the assistance-in-progress notification filter confirms the assistance state, and when being assistance in progress, the notification is stopped. The toilet sensor 10 can reduce unnecessary notification to the caregiver by the assistance-in-progress notification filter, and can prevent the caregiver from rushing to the toilet assistance that does not need to be responded. In addition, a notification type such as alert notification, normal notification, or not notify can be set to each notification for each care recipient, and a setting according to status of the care recipient can be made, such as set to the alert notification in a case of a care recipient requiring care assistance and the normal notification in a case of a care recipient for which watching is a purpose.

When a person specified by the person authentication processing is a caregiver, the toilet sensor 10 detects entry/exit of the caregiver, and performs notification to another caregiver. Since the entry notification of a caregiver is performed to notify another caregiver that the caregiver has rushed to the toilet assistance for a care recipient, when the caregiver enters the toilet where the care recipient is entering, the notification is performed to the another caregiver. When the care recipient has not entered, entry information of the caregiver is maintained and no notification is performed. With this notification, the another caregiver is informed that the caregiver has rushed to assist the care recipient. In addition, the caregiver can notify the another caregiver that he/she will rush to assist with respect to the toilet entry notification of the care recipient, and when the caregiver cannot rush after performing the rush notification to the another caregiver, the caregiver can notify rush stop. By the rush notification, it is possible to prevent waste of rushing, by the caregiver, to the toilet of the same care recipient, and by the rush stop notification, it is possible to prevent the care recipient from being left unattended when the caregiver cannot rush to the toilet of the care recipient after the rush notification.

These notifications are also performed from the toilet sensor 10 to the server 40 through a network, and are finally notified to the caregiver. In addition, also for these notifications, presence or absence of notification and the importance ("alert notification" "normal notification") can be set for each care recipient as a notification condition. Although details are not described, the notification condition can be set for each caregiver according to a degree of skill or the like of the caregiver. For example, such a setting can be beneficial in a case where a skilled caregiver can handle with one person, but a non-skilled caregiver needs to handle with two persons, or the like.

In the above, the present system has been described on the premise that there is only one toilet bowl 20 (only one toilet room). However, in the present system, it is preferred to acquire, for a plurality of toilets, excretion information for detection of a detection event, entry/exit information, leaving/sitting information, and an authentication result. With this, the present system can also be applied even when a certain person to be assisted may use two or more toilets.

In addition, in a case of a facility such as a hospital, the server 40 can be installed in the facility, and in a case of personal use, the server 40 can be installed in a private house or an apartment house. In either case, the server 40 can also be a cloud server.

In addition, a program of the terminal apparatus 50 can be incorporated in the terminal apparatus 50 in such a way as to be executable as care software including a notification function of notification information. In addition to the notification information, the terminal apparatus 50 can also directly (or directly and automatically) receive and store information acquired on a toilet side such as the toilet sensor 10, and can also receive and store various information recorded by the server 40 in the same manner.

Of course, also in the present example embodiment, a function described as the function of the server 40 is provided on a toilet sensor 10 side without using the server 40, thereby the toilet sensor 10 alone can be configured in such a way as to perform notification to the terminal apparatus 50.

As described above, in the present example embodiment, an entry/exit sensor, a sitting sensor, an excretion identification sensor, and communication equipment are attached to a toilet seat, a state of a care recipient inside a toilet is recognized, and the recognized state is transmitted to a caregiver through the communication equipment. The present system specifies an individual by person authentication processing, and notifies the caregiver of an entry notification, an exit notification, a sitting notification, a leaving notification, an excretion start notification, and an excretion completion notification. In the notification, presence or absence of notification and importance can be set for each care recipient, the importance of notification can be changed according to a state of the care recipient, so that the caregiver can use to make determination when the caregiver rushes to toilet assistance. When a caregiver rushes to toilet assistance of a care recipient, a caregiver rush notification is performed to another caregiver, and when the caregiver cannot rush to the toilet assistance after the caregiver rush notification, a caregiver rush stop notification is performed to the another caregiver. In addition, when the caregiver rushes to the toilet assistance of the care recipient, the present system performs a caregiver entry notification, and an assistance state is changed to assistance in progress. In a case of an assistance-in-progress state, events detected by each sensor of the present system may not be notified to another caregiver. The caregiver can confirm excretion status of the care recipient from the notification, and utilize to promote the care recipient to excrete. In addition, the present system can provide a function of notifying a caregiver of an alarm when detecting other than excrement.

In the present example embodiment, these functions reduce a burden on a caregiver to monitor a toilet, and enable a care recipient to receive a heavy support. Specifically, first to fifth problems related to excretion management and excretion assistance can be solved as follows.

At first, the first problem can be solved as follows. Since a caregiver can confirm that a care recipient in charge has entered a toilet by receiving a toilet entry notification, it is not necessary to confirm whether the care recipient goes to the toilet every time when the care recipient moves. Even when the care recipient goes to the toilet without being seen by the caregiver, the caregiver can recognize entry to the toilet and rush to assist the care recipient. In addition, the caregiver can recognize status of the care recipient in the toilet by raising notification of sitting/leaving on a toilet seat and a start/end of excretion. Thus, it is also possible to move away from a side of the toilet during excretion of the care recipient who needs assistance before and after the excretion, and to confirm a scene of another care recipient. By receiving the notification from the toilet sensor 10 in this manner, it is possible to reduce a time and labor required for monitoring the toilet by the caregiver.

The second problem can be solved as follows. When a care recipient who is unable to hold a sitting position or standing position enters a toilet alone, the toilet sensor 10 performs a notification on a caregiver. A toilet entry notification, a toilet sitting notification, and a toilet excretion start notification include information such as information identifying the toilet sensor 10 that has made the notification and the care recipient during toilet use, and a date and time. Therefore, the caregiver can recognize information of the toilet that has entered with the care recipient by confirming the toilet entry notification, the toilet sitting notification, and the toilet excretion start notification, and can rush to assist. As a result, since the caregiver can rush to the care recipient in a short time, it is possible to prevent the care recipient from leaking in the toilet, and to prevent the care recipient from unreasonable movement or standing by himself/herself and thereby prevent injury due to a fall. In addition, it is possible to prevent the caregiver from not rushing to assist in excretion. In addition, with regard to a care recipient such as a person who cannot wipe by himself/herself, or a person who cannot take out or wear clothes, it is possible to recognize an end of excretion by a toilet excretion end notification even when the caregiver is outside the toilet, and therefore, even when the care recipient is unable to inform the caregiver of the end of the excretion, it is possible to prevent the care recipient from remaining sitting. Further, when the care recipient sits down, a long-time sitting timer is set for each care recipient, and when the care recipient remains sitting for a long time, a long-time sitting notification is performed to the caregiver. Thus, when abnormality occurs in the care recipient and the care recipient remains sitting, the caregiver can immediately rush. When a care recipient who is difficult to walk or hold a standing position leaves the toilet seat or exits the toilet, the caregiver can immediately rush to the toilet by a toilet leaving notification or a toilet exit notification, so that it is possible to prevent the care recipient from keeping waiting in the vicinity of the toilet. As described above, since status of the care recipient is notified to the caregiver by the notification, status in which the care recipient cannot receive assistance is not occurred, and thus the problem can be solved.

The third problem can be solved as follows. The toilet sensor 10 performs a caregiver toilet entry notification when a caregiver enters a toilet while a care recipient enters the toilet, and performs a caregiver toilet exit notification when the caregiver exits the toilet while the care recipient enters the toilet. With this notification, it is possible to inform another caregiver that the caregiver is assisting the care recipient in the toilet, so that it is possible to eliminate useless rushing of the caregiver. In addition, the caregiver can inform another caregiver that the caregiver will rush to toilet assistance of the care recipient by a caregiver toilet rush notification. As a result, it is possible to prevent an unnecessary caregiver from rushing to the care recipient in assistance in progress. When the caregiver cannot rush after the caregiver toilet rush notification, the caregiver can inform another caregiver by a caregiver toilet rush stop notification. Accordingly, when the caregiver cannot rush, it is possible to prevent the another caregiver from not rushing to the toilet of the care recipient. Since the caregiver can confirm the number of caregivers who are assisting the toilet or who are rushing to assist, the caregiver can rush to assist the care recipient who needs assistance by a plurality of persons. In this way, it is possible to share care assistance status among the caregivers by the notification, so that the problem can be solved.

The fourth problem can be solved as follows. The toilet entry notification and the toilet exit notification performed by the toilet sensor 10 include information such as a toilet entry/exit time of a care recipient, and the toilet sitting notification and the toilet leaving notification include information such as a sitting/leaving time of a toilet bowl of the care recipient. In addition, the toilet excretion start notification performed by the toilet sensor 10 includes information such as an excretion start time and a type of excretion, and the toilet excretion end notification includes an excretion end time and a result of identification of excretion. Since these pieces of information include information necessary for an excretion record of the care recipient, when there is a notification of the toilet sensor 10, the caregiver does not need to directly confirm excretion of the care recipient or hear the care recipient for the excretion record. As a result, it is possible to reduce a burden on the excretion record by the caregiver. In addition, the caregiver can recognize toilet use status of the care recipient by the toilet entry notification and the toilet excretion start notification. Therefore, since the caregiver can easily specify a care recipient who does not use the toilet, it is possible to reduce a time and effort required for confirming the excretion status, and it is possible to promote the excretion without a burden. In this way, it is possible to solve the problem of confirming the excretion status by the notification from the toilet sensor 10.

The fifth problem can be solved as follows. When a foreign body other than excrement is detected in a toilet bowl during excretion of a care recipient, the toilet sensor 10 performs a foreign body detection notification and notifies a caregiver that there is a foreign body in the toilet bowl. With this notification, the caregiver can recognize that the care recipient has dropped a diaper or a urine absorbing pad into the toilet bowl, so that the caregiver can handle a problem before the foreign body is flushed. As a result, it is not necessary for a care facility to perform foreign body removal asked to a piping contractor, and thereby it is possible to prevent a situation in which a facility related to drainage cannot be operated.

In the present example embodiment, in addition to the function of solving these problems, in a state where a droplet of excrement, dust, or the like adhere to the toilet sensor 10 and a sensor becomes dirty, and detection of a start and end of excretion cannot be performed, in order to prevent a care recipient from using a toilet, a sensor dirty notification is performed to a caregiver when dirt of the sensor is detected. In addition, when abnormality of the toilet sensor 10 is solved, a service recovery notification is performed in order to notify the caregiver of the recovery. By the service recovery notification, the caregiver can immediately recognize that the abnormality of the toilet sensor 10 has been solved, so that it is possible to reduce a time and effort to confirm whether the abnormality has been solved, and thus it is possible to shorten a use stop time of the toilet sensor 10.

As described above, the present system can achieve an advantageous effect described in the first example embodiment. In particular, the present system has the following advantageous effects.

The first advantageous effect is that the toilet sensor 10 detects an event (entry, sitting, a start of excretion, an end of excretion, leaving, exit) from toilet entry to toilet exit of a care recipient, notifies a caregiver of the event, and thereby it is possible to reduce a burden on monitoring a toilet by the caregiver.

The second advantageous effect is that, in a toilet use notification to which the toilet sensor 10 performs notification, presence or absence of notification and importance can be set for each care recipient, the caregiver can confirm necessity of assistance, based on the importance of the notification, and therefore toilet assistance work can be efficiently performed.

The third advantageous effect is that, when a care recipient who needs assistance enters a toilet alone, a notification is received from the toilet sensor 10 to a caregiver in an operation that the care recipient needs assistance, and thereby it is possible to prevent the care recipient from keeping waiting for the caregiver, injuring due to unreasonable movement, and the like.

A fourth advantageous effect is that, when a care recipient is in a dangerous state in a toilet during excretion, a caregiver can recognize, by a notification, that the care recipient remains sitting for a long time or that the care recipient has not exit from the toilet, and therefore the caregiver can promptly respond to the care recipient who has experienced abnormality in the toilet.

The fifth advantageous effect is that, when a caregiver enters a toilet in which a care recipient is entering, the toilet sensor 10 performs a caregiver entry notification, and a state of the care recipient is set to an assistance-in-progress state. In a case of the assistance-in-progress state, by not notifying another caregiver, it is possible to prevent the caregiver from wasting rush, and it is possible to improve efficiency of toilet assistance work.

The sixth advantageous effect is that, when a caregiver confirms toilet use by a care recipient who needs assistance, the caregiver can inform, by a caregiver rush notification, another caregiver that the caregiver will rush to the assistance. With this notification, it is possible to prevent an unnecessary caregiver from rushing to assist the care recipient in the toilet, and thus it is possible to improve efficiency of the toilet assistance work.

The seventh advantageous effect is that, since it is possible to recognize excretion status of a care recipient without hearing presence or absence of the excretion from the care recipient, it is possible to reduce a burden on a caregiver to hear. In addition, since it is possible to recognize the excretion status, it is possible to easily promote excretion to the care recipient who has not excreted.

The eighth advantageous effect is that, by notifying a caregiver of an alarm when detecting other than excrement in a toilet bowl, an accident of flushing a solid body such as a diaper or a urine absorbing pad into a drain pipe of a toilet can be prevented, drainage pipe construction by a contractor which has been performed so far is unnecessary, and therefore reduction of a maintenance cost can be achieved.

Another Example Embodiment

[a]
Although a function of an information processing system and each apparatus included in the system have been described in each example embodiment, each apparatus is not limited to an illustrated configuration example, and the function may be achieved as each apparatus.

Figure 15:
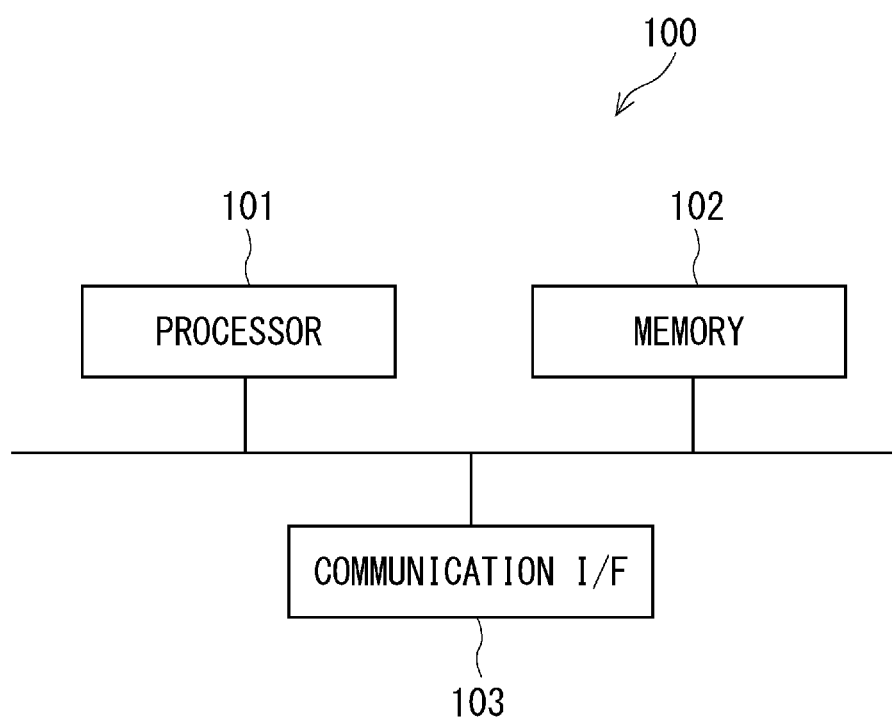
FIG. 15 is a diagram illustrating one example of a hardware configuration of an apparatus.

[b]
Each apparatus according to the first and second example embodiments may have the following hardware configuration. FIG. 15 is a diagram illustrating one example of a hardware configuration of an apparatus. Note that, the same applies to the above-described another example embodiment [a].

An apparatus 100 illustrated in FIG. 15 can include a processor 101, a memory 102, and a communication interface (I/F) 103. The processor 101 may be, for example, a microprocessor, a micro processor unit (MPU), a CPU, or the like. The processor 101 may include a plurality of processors. The memory 102 is configured by, for example, a combination of a volatile memory and a non-volatile memory. The function of each apparatus described in the first and second example embodiments is achieved by the processor 101 reading and executing a program stored in the memory 102. At this time, transmission and reception of information to and from another apparatus can be performed via the communication interface 103 or a not-illustrated input/output interface.

In the example described above, the program may be stored by using various types of non-transitory computer-readable media, and supplied to a computer. The non-transitory computer-readable medium includes various types of tangible storage media. Examples of non-transitory computer-readable medium include a magnetic recording medium (e.g., a flexible disk, a magnetic tape, and a hard disk drive), and a magneto-optical recording medium (e.g., a magneto-optical disk). Further, this example includes a CD-read only memory (ROM), a CD-R, and a CD-R/W. Furthermore, this example includes a semiconductor memory (e.g., a mask ROM, a programmable ROM (PROM), an erasable PROM (EPROM), a flash ROM, and a random access memory (RAM)). In addition, the program may also be supplied to the computer by various types of transitory computer-readable media. Examples of transitory computer-readable medium include an electric signal, an optical signal, and an electromagnetic wave. The transitory computer-readable medium can supply the program to the computer via a wired communication path such as an electric wire and an optical fiber, or a wireless communication path.

[c]
Further, in each of the above-described example embodiments, as an example of a procedure of an information processing method in an information processing system, the present disclosure may also adopt a form as an information processing method. The information processing method includes an acquisition step, a first detection step, a second detection step, an authentication step, a storage step, and an output step as follows. The acquisition step acquires excretion information indicating at least a start and end of excretion, based on imaging data captured by an image capture apparatus installed in such a way as to include, in an image capture range, an excretion range of excrement in a toilet bowl of a toilet. In the first detection step, a first sensor detects entry/exit of a person to/from the toilet. In the second detection step, a second sensor detects leaving/sitting on a toilet seat installed in the toilet bowl. The authentication step authenticates a person who has performed entry/exit to/from the toilet, and also determines whether the person is a person to be assisted as a user of the toilet or a helper who assists the user. The storage step stores a notification condition. The output step outputs notification information to a notification destination, based on a detection event indicated by the excretion information acquired in the acquisition step, entry/exit information detected by the first sensor, leaving/sitting information detected by the second sensor, and an authentication result in the authentication step, and the notification condition. The storage step stores, as the notification condition, necessity of notification, and the notification information and the notification destination when notification is necessary, for each of the detection events. Note that, another example is similar to those described in each of the above-described example embodiments. In addition, it can be said that the program is a program for causing a computer to execute processing of including the acquisition step, the first detection step, the second detection step, the authentication step, the storage step, and the output step.

Note that, the present disclosure is not limited to the above-described example embodiment, and can be appropriately modified without departing from the spirit thereof. In addition, the present disclosure may be implemented by appropriately combining each of the example embodiments.

Some or all of the above-described example embodiments may be described as the following supplementary notes, but are not limited thereto.

<Supplementary Note>
(Supplementary Note 1)
An information processing system comprising:
an acquisition unit for acquiring excretion information indicating at least a start and an end of excretion, based on imaging data captured by an image capture apparatus installed in such a way as to include, in an image capture range, an excretion range of excrement in a toilet bowl of a toilet;
a first sensor configured to detect entry/exit of a person to/from the toilet;
a second sensor configured to detect leaving and sitting on a toilet seat installed on the toilet bowl;
an authentication unit for authenticating a person who has performed entry/exit to/from the toilet, and also determining whether the person is a person to be assisted as a user of the toilet or a helper who assists the user;
a storage unit for storing a notification condition; and
an output unit for outputting notification information to a notification destination, based on a detection event indicated by the excretion information acquired by the acquisition unit, entry/exit information detected by the first sensor, leaving/sitting information detected by the second sensor, and an authentication result in the authentication unit, and the notification condition, wherein the storage unit stores, as the notification condition, necessity of notification, and the notification information and the notification destination when notification is necessary, for each of the detection events.

(Supplementary Note 2)

The information processing system according to Supplementary Note 1, wherein the notification condition includes importance information indicating importance of notification, and the output unit outputs the notification information in a state including the importance information or in a state indicating the importance information.

(Supplementary Note 3)

The information processing system according to Supplementary Note 1 or 2, wherein the storage unit stores, as the notification condition, necessity of notification, and the notification information and the notification destination when notification is necessary, for each of the detection events and each person to be assisted as the user.

(Supplementary Note 4)

The information processing system according to any one of Supplementary Notes 1 to 3, wherein the detection event includes a first event being an event in which a person to be assisted as the user is sitting on the toilet seat for a certain period of time or more, and, as the notification condition with respect to the first event, the notification destination includes a contact address of a helper who assists the user, and the notification information includes an alert for requesting assistance.

(Supplementary Note 5)

The information processing system according to any one of Supplementary Notes 1 to 4, wherein the acquisition unit acquires, as at least a part of the excretion information, information indicating whether the imaging data captured by the image capture apparatus includes a foreign body being an object other than feces and urine as a subject excluding the toilet bowl and washing liquid for the toilet bowl, the detection event includes a second event being an event in which the foreign body is detected, and, as the notification condition with respect to the second event, the notification destination includes a contact address of a helper who assists a person to be assisted as the user, and the notification information includes an alert for requesting removal of the foreign body.

(Supplementary Note 6)

The information processing system according to any one of Supplementary Notes 1 to 5, wherein the detection event includes a third event being an event in which dirt is detected in at least one of the image capture apparatus, the first sensor, and the second sensor, and, as the notification condition with respect to the third event, the notification destination includes a contact address of a person who can become the helper, and the notification information includes an alert for requesting removal of the dirt.

(Supplementary Note 7)

The information processing system according to any one of Supplementary Notes 1 to 6, wherein the detection event includes a fourth event being an event in which it is detected that the helper enters the toilet while a person to be assisted as the user enters the toilet, as the notification condition with respect to the fourth event, the notification destination includes a contact address of a person who can become the helper other than the helper related to the fourth event, and the notification information includes information notifying that a person to be assisted as the user is being assisted, and, when the fourth event occurs, the output unit does not perform notification related to another specific detection event even when the another specific detection event occurs, until at least a state indicated by the fourth event disappears.

(Supplementary Note 8)

The information processing system according to any one of Supplementary Notes 1 to 7, further comprising a reception unit for receiving, from a person who can become the helper, rush information for notifying a person who can become another helper of rushing for assisting the user, wherein the detection event includes a fifth event indicating that the reception unit has received the rush information, and, as the notification condition with respect to the fifth event, the notification destination includes a contact address of a person who can become the another helper, and the notification information includes information for notifying of rushing for assisting a person to be assisted as the user.

(Supplementary Note 9)

The information processing system according to any one of Supplementary Notes 1 to 8, further comprising a setting unit for setting the notification condition.

(Supplementary Note 10)

An information processing apparatus that comprises an image capture apparatus, and is installed in a toilet bowl in such a way that the image capture apparatus is arranged in such a way as to include, in an image capture range, an excretion range of excrement in the toilet bowl of a toilet, the information processing apparatus comprising:

an acquisition unit for acquiring excretion information indicating at least a start and an end of excretion, based on imaging data captured by the image capture apparatus;

a first sensor configured to detect entry/exit of a person to/from the toilet;

a second sensor configured to detect leaving and sitting on a toilet seat installed on the toilet bowl;

an authentication unit for authenticating a person who has performed entry/exit to/from the toilet, and also determining whether the person is a person to be assisted as a user of the toilet or a helper who assists the user;

a storage unit for storing a notification condition; and an output unit for outputting notification information to a notification destination, based on a detection event indicated by the excretion information acquired by the acquisition unit, entry/exit information detected by the first sensor, leaving/sitting information detected by the second sensor, and an authentication result in the authentication unit, and the notification condition, wherein the storage unit stores, as the notification condition, necessity of notification, and the notification information and the notification destination when notification is necessary, for each of the detection events.

(Supplementary Note 11)

An information processing method comprising:

an acquisition step of acquiring excretion information indicating at least a start and an end of excretion, based on imaging data captured by an image capture apparatus installed in such a way as to include, in an image capture range, an excretion range of excrement in a toilet bowl of a toilet;
a first detection step of detecting, by a first sensor, entry/exit of a person to/from the toilet;
a second detection step of detecting, by a second sensor, leaving and sitting on a toilet seat installed on the toilet bowl;
an authentication step of authenticating a person who has performed entry/exit to/from the toilet, and also determining whether the person is a person to be assisted as a user of the toilet or a helper who assists the user;
a storage step of storing a notification condition; and
an output step of outputting notification information to a notification destination, based on a detection event indicated by the excretion information acquired in the acquisition step, entry/exit information detected by the first sensor, leaving/sitting information detected by the second sensor, and an authentication result in the authentication step, and the notification condition,
wherein the storage step stores, as the notification condition, necessity of notification, and the notification information and the notification destination when notification is necessary, for each of the detection events.

(Supplementary Note 12)

A program for causing a computer to execute processing including:
an acquisition step of acquiring excretion information indicating at least a start and an end of excretion, based on imaging data captured by an image capture apparatus installed in such a way as to include, in an image capture range, an excretion range of excrement in a toilet bowl of a toilet;
a first detection step of detecting, by a first sensor, entry/exit of a person to/from the toilet;
a second detection step of detecting, by a second sensor, leaving and sitting on a toilet seat installed on the toilet bowl;
an authentication step of authenticating a person who has performed entry/exit to/from the toilet, and also determining whether the person is a person to be assisted as a user of the toilet or a helper who assists the user;
a storage step of storing a notification condition; and
an output step of outputting notification information to a notification destination, based on a detection event indicated by the excretion information acquired in the acquisition step, entry/exit information detected by the first sensor, leaving/sitting information detected by the second sensor, and an authentication result in the authentication step, and the notification condition,
wherein the storage step stores, as the notification condition, necessity of notification, and the notification information and the notification destination when notification is necessary, for each of the detection events.

Although the invention of the present application has been described with reference to the example embodiments, the invention of the present application is not limited to the above. Various modifications that can be understood by a person skilled in the art within the scope of the invention can be made to the configuration and details of the invention of the present application.

This application is based upon and claims the benefit of priority from Japanese patent application No. 2020-204674, filed on Dec. 10, 2020, the disclosure of which is incorporated herein in its entirety by reference.

REFERENCE SIGNS LIST

1 INFORMATION PROCESSING SYSTEM
1a ACQUISITION UNIT
1b FIRST SENSOR
1c SECOND SENSOR
1d AUTHENTICATION UNIT
1e STORAGE UNIT
1f OUTPUT UNIT
10 INFORMATION PROCESSING APPARATUS (TOILET SENSOR)
11 SECOND EXTERNAL BOX
11a CPU
11b CONNECTOR
11c, 11d USB I/F
12 INTER-BOX CONNECTION UNIT
13 FIRST EXTERNAL BOX
14a WiFi MODULE
14b BLUETOOTH MODULE
15a HUMAN DETECTING SENSOR
15b SECOND CAMERA
16a RANGE SENSOR
16b FIRST CAMERA
20 TOILET BOWL
21 BODY
22 TOILET SEAT
23 TOILET SEAT COVER
30 TOILET BOWL WITH INFORMATION PROCESSING APPARATUS
40 SERVER
41 CONTROL UNIT
42 STORAGE UNIT
50 TERMINAL APPARATUS
51 DISPLAY SCREEN
52, 53, 54 NOTIFICATION INFORMATION
52a INFORMATION INDICATING IMPORTANCE
52b BUTTON
100 APPARATUS
101 PROCESSOR
102 MEMORY
103 COMMUNICATION INTERFACE

What is claimed is:

1. An information processing system comprising:
at least one memory storing instructions and a notification condition;
at least one processor configured to execute the instructions to do information processing, the information processing includes acquiring excretion information indicating at least a start and an end of excretion, based on imaging data captured by an image capture apparatus installed in such a way as to include, in an image capture range, an excretion range of excrement in a toilet bowl of a toilet;
a first sensor configured to detect entry/exit of a person to/from the toilet; and
a second sensor configured to detect leaving and sitting on a toilet seat installed on the toilet bowl, wherein
the information processing further includes
authenticating a person who has performed entry/exit to/from the toilet, and also determining whether the person is a person to be assisted as a user of the toilet or a helper who assists the user,
outputting notification information to a notification destination, based on a detection event indicated by the excretion information acquired by the acquiring, entry/exit information detected by the first sensor, leaving/sitting information detected by the second sensor, and an authentication result in the authenticating, and the notification condition, and, the at least one memory stores, as the notification condition, necessity of notification, and the notification information and the notification destination when notification is necessary, for each of the detection events.

2. The information processing system according to claim 1, wherein the notification condition includes importance information indicating importance of notification, and the outputting is outputting the notification information in a state including the importance information or in a state indicating the importance information.

3. The information processing system according to claim 1, wherein the at least one memory stores, as the notification condition, necessity of notification, and the notification information and the notification destination when notification is necessary, for each of the detection events and each person to be assisted as the user.

4. The information processing system according to claim 1, wherein the detection event includes a first event being an event in which a person to be assisted as the user is sitting on the toilet seat for a certain period of time or more, and, as the notification condition with respect to the first event, the notification destination includes a contact address of a helper who assists the user, and the notification information includes an alert for requesting assistance.

5. The information processing system according to claim 1, wherein the acquiring is acquiring, as at least a part of the excretion information, information indicating whether the imaging data captured by the image capture apparatus includes a foreign body being an object other than feces and urine as a subject excluding the toilet bowl and washing liquid for the toilet bowl, the detection event includes a second event being an event in which the foreign body is detected, and, as the notification condition with respect to the second event, the notification destination includes a contact address of a helper who assists a person to be assisted as the user, and the notification information includes an alert for requesting removal of the foreign body.

6. The information processing system according to claim 1, wherein the detection event includes a third event being an event in which dirt is detected in at least one of the image capture apparatus, the first sensor, and the second sensor, and, as the notification condition with respect to the third event, the notification destination includes a contact address of a person who can become the helper, and the notification information includes an alert for requesting removal of the dirt.

7. The information processing system according to claim 1, wherein the detection event includes a fourth event being an event in which it is detected that the helper enters the toilet while a person to be assisted as the user enters the toilet, as the notification condition with respect to the fourth event, the notification destination includes a contact address of a person who can become the helper other than the helper related to the fourth event, and the notification information includes information notifying that a person to be assisted as the user is being assisted, and, when the fourth event occurs, the outputting is not executed notification related to another specific detection event even when the another specific detection event occurs, until at least a state indicated by the fourth event disappears.

8. The information processing system according to claim 1, wherein the information processing further includes receiving, from a person who can become the helper, rush information for notifying a person who can become another helper of rushing for assisting the user, the detection event includes a fifth event indicating that the rush information has been received by the receiving, and, as the notification condition with respect to the fifth event, the notification destination includes a contact address of a person who can become the another helper, and the notification information includes information for notifying of rushing for assisting a person to be assisted as the user.

9. The information processing system according to claim 1, wherein the information processing further includes setting the notification condition.

10. The information processing system according to claim 1, further comprising the image capture apparatus.

11. An information processing method comprising:

acquiring excretion information indicating at least a start and an end of excretion, based on imaging data captured by an image capture apparatus installed in such a way as to include, in an image capture range, an excretion range of excrement in a toilet bowl of a toilet;

detecting, by a first sensor, entry/exit of a person to/from the toilet;

detecting, by a second sensor, leaving and sitting on a toilet seat installed on the toilet bowl;

authenticating a person who has performed entry/exit to/from the toilet, and also determining whether the person is a person to be assisted as a user of the toilet or a helper who assists the user;

storing a notification condition; and outputting notification information to a notification destination, based on a detection event indicated by the excretion information acquired in the acquiring, entry/exit information detected by the first sensor, leaving/sitting information detected by the second sensor, and an authentication result in the authenticating, and the notification condition, wherein the storing includes storing, as the notification condition, necessity of notification, and the notification information and the notification destination when notification is necessary, for each of the detection events.

12. A non-transitory computer-readable medium storing a program for causing a computer to execute processing including:

acquiring excretion information indicating at least a start and an end of excretion, based on imaging data captured by an image capture apparatus installed in such a way as to include, in an image capture range, an excretion range of excrement in a toilet bowl of a toilet;

detecting, by a first sensor, entry/exit of a person to/from the toilet;

detecting, by a second sensor, leaving and sitting on a toilet seat installed on the toilet bowl;

authenticating a person who has performed entry/exit to/from the toilet, and also determining whether the person is a person to be assisted as a user of the toilet or a helper who assists the user;

storing a notification condition; and outputting notification information to a notification destination, based on a detection event indicated by the excretion information acquired in the acquiring, entry/exit information detected by the first sensor, leaving/sitting information detected by the second sensor, and an authentication result in the authenticating, and the notification condition, wherein the storing includes storing, as the notification condition, necessity of notification, and the notification information and the notification destination when notification is necessary, for each of the detection events.

* * * * *